United States Patent
Kwon et al.

(10) Patent No.: US 11,489,184 B2
(45) Date of Patent: Nov. 1, 2022

(54) ELECTROLYTE INCLUDING MIXTURE OF ACTIVE MATERIAL AND PRECURSOR THEREOF

(71) Applicant: Foundation for Research and Business, Seoul National University of Science and Technology, Seoul (KR)

(72) Inventors: Yong Chai Kwon, Seoul (KR); Won Mi Lee, Gyeonggi-do (KR); Gyun Ho Park, Gyeongsangbuk-do (KR)

(73) Assignee: Foundation for Research and Business, Seoul National University of Science and Technology, Seoul (KR)

( * ) Notice: Subject to any disclaimer, the term of this patent is extended or adjusted under 35 U.S.C. 154(b) by 0 days.

(21) Appl. No.: 17/213,282

(22) Filed: Mar. 26, 2021

(65) Prior Publication Data
US 2021/0305610 A1    Sep. 30, 2021

(30) Foreign Application Priority Data
Mar. 26, 2020    (KR) .................. 10-2020-0037077

(51) Int. Cl.
*H01M 8/08*      (2016.01)
*C07C 50/32*     (2006.01)
*C07C 309/44*    (2006.01)
*H01M 8/18*      (2006.01)

(52) U.S. Cl.
CPC .............. *H01M 8/08* (2013.01); *C07C 50/32* (2013.01); *C07C 309/44* (2013.01); *H01M 8/188* (2013.01); *C07C 2602/10* (2017.05); *H01M 2300/0002* (2013.01)

(58) Field of Classification Search
CPC .......... H01M 8/08; H01M 8/18; H01M 8/188
See application file for complete search history.

(56) References Cited

U.S. PATENT DOCUMENTS

| | | | |
|---|---|---|---|
| 2009/0297890 A1* | 12/2009 | Shimomura | H01M 8/16 429/2 |
| 2015/0236543 A1* | 8/2015 | Brushett | H01M 4/58 429/105 |
| 2016/0248114 A1* | 8/2016 | Huskinson | B29C 48/2528 |
| 2019/0393506 A1 | 12/2019 | Hartwig et al. | |

FOREIGN PATENT DOCUMENTS

| | | |
|---|---|---|
| JP | 2017-071714 | 4/2017 |
| KR | 10-2018-0044001 | 5/2018 |
| KR | 10-2018-0080209 | 7/2018 |
| KR | 10-2018-0134369 | 12/2018 |
| KR | 10-2019-0072585 | 6/2019 |
| WO | WO 2015/048550 | 4/2015 |
| WO | WO 2017/137730 | 8/2017 |

OTHER PUBLICATIONS

Lee et al. "Alkaline Aqueous Organic Redox Flow Batteries of High Energy and Power Densities Using Mixed Naphthoquinone Derivatives", Chemical Engineering Journal, 386: 123985-1-123985-10, Available Online Dec. 30, 2019.

Tong et al. "Molecular Engineering of an Alkaline Naphthoquinone Flow Battery", ACS Energy Letters, 4(8): 1880-1887, Published Online Jul. 11, 2019.

* cited by examiner

*Primary Examiner* — Karie O'neill Apicella

(57) ABSTRACT

An electrolyte including a mixture of hydroxynaphtoquinone and a precursor material thereof is provided. The electrolyte may achieve higher capacities.

9 Claims, 18 Drawing Sheets

ELECTROLYTE INCLUDING MIXTURE OF ACTIVE MATERIAL AND PRECURSOR THEREOF

RELATED APPLICATIONS

This application claims the benefit of priority of Korean Patent Application No. 10-2020-0037077 filed on Mar. 26, 2020, the contents of which are incorporated herein by reference in their entirety.

FIELD AND BACKGROUND OF THE INVENTION

The present disclosure relates to an electrolyte including a mixture of an active material and a precursor thereof, and an aqueous redox flow battery using the same.

Redox flow batteries (RFBs) are a large-scale energy storage device and are attracting attention as a key technology for renewable energy such as solar energy and wind energy. Unlike general lithium or sodium secondary batteries, the RFBs have the mechanism in which active materials are dissolved in an electrolyte solution, and the active materials undergo a redox reaction in each of the positive electrode and the negative electrode, resulting in a capacity to be charged and discharged. The capacity of the redox flow batteries is determined by the redox reaction of the electrolytes supplied from an external storage, and therefore the batteries have an advantage that the capacity of the entire batteries may be adjusted by controlling the size of the external storage. In addition, since the redox reaction of the redox couple which is an active material, occurs on the surfaces of the positive electrode and the negative electrode, the batteries have an advantage of being longer lifespan compared to general batteries such as lithium-ion batteries undergoing the reaction in which ions are intercalated/deintercalated into/from the electrode active material.

The RFBs may be divided into aqueous RFBs and non-aqueous RFBs depending on the type of electrolyte solvents containing redox active materials. Aqueous redox flow batteries (ARFBs) using water as a solvent for the electrolyte have advantages in terms of high ion conductivity, stability, and economy. Meanwhile, with respect to active materials for RFBs, various types of active materials such as metal active materials, organic active materials, and organometallic active materials have been used. However, when an organic active material is used for the ARFBs, since the organic active material has a low solubility in water, various studies have been conducted to increase the solubility.

Under this background, the present inventors discovered that when a mixture of an active material having a hydroxynaphthoquinone structure and a precursor thereof is used as an electrolyte, a higher solubility and electrode performance are obtained, and completed the present disclosure.

RELATED ART DOCUMENT

Patent Document

[Patent Document 1] Korean Laid—Open Patent Publication No. 10-2018-0044001 (May 2, 2018)

SUMMARY OF THE INVENTION

The present disclosure provides a hydroxynaphthoquinone-containing electrolyte having a high solubility and electrochemical performance.

According to an aspect, there is provided an electrolyte for an aqueous redox flow battery (ARFB) which includes a compound represented by Formula (I) and a compound represented by Formula (II):

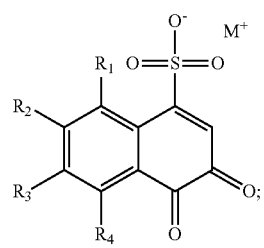

[Formula (I)]

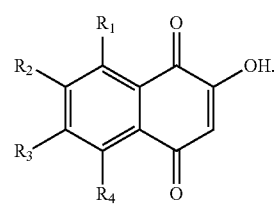

[Formula (II)]

In Formulas (I) and (II), $R_1$ to $R_4$ is each independently selected from a group consisting of hydrogen, halogen, $C_1$-$C_3$ alkyl, and $C_1$-$C_3$ alkoxy, M is a metal selected from a group consisting of Na, Li, and K.

Further, according to another aspect, there is provided an ARFB including the electrolyte for the ARFB.

Hereinafter, the present disclosure will be described in detail.

It is understood that the term "about" refers to a range of numbers that one of ordinary skill in the art would consider equivalent to the stated value in terms of achieving the same function or result.

All numerical ranges given throughout this specification include their upper and lower limits, and all narrower numerical ranges falling within such ranges, and all of the narrower numerical ranges are considered to be clearly and specifically set forth herein.

In the prior art, when hydroxynaphthoquinone is used as an active material of an ARFB, it is difficult to achieve a high battery capacity because hydroxynaphthoquinone has a low solubility in water. Accordingly, the present inventors found that when an electrolyte containing a mixture of a hydroxynaphthoquinone derivative and a precursor material thereof is used as an active material, a higher solubility may be obtained, and as a result, a high electrode capacity may be achieved, and completed the present disclosure. The present disclosure is based on this finding.

The electrolyte for an ARFB according to the present disclosure may include a mixture of the compounds represented by Formulas (I) and (II). The compound represented by Formula (I) may be a precursor material of the compound represented by Formula (II).

In the compounds represented by Formulas (I) and (II), $R_1$ to $R_4$ may be each independently selected from a group consisting of hydrogen, halogen, $C_1$-$C_3$ alkyl, and $C_1$-$C_3$ alkoxy, and may be preferably selected from a group consisting of hydrogen, halogen, methyl, ethyl, propyl, isopropyl, methoxy, ethoxy, propoxy, and isopropoxy. More specifically, $R_1$ to $R_4$ may be each independently selected from a group consisting of hydrogen, halogen, methyl, ethyl, propyl and isopropyl, and may be more preferably hydrogen or halogen. Since the compound represented by Formula (I) is a precursor material of the compound represented by Formula (II), $R_1$ to $R_4$ in Formula (I) are the same as $R_1$ to $R_4$ in Formula (II), respectively. $R_1$ to $R_4$ do not participate in the conversion reaction from the compound represented by Formula (I) to the compound represented by Formula (II), and therefore they have the same structure.

In Formula (I), M may be a metal selected from a group consisting of Na, Li and K.

A cation of M (i.e. $M^+$) may be an inert, stable cation that does not participate in the redox reaction. Preferably, M may be Na.

A molar ratio of the compound represented by Formula (II) to the compound represented by Formula (I) may range from 0.1 to 10. Preferably, the compound represented by Formula (I) may be included at a molar concentration less than the compound represented by Formula (II). The molar ratio of the compound represented by Formula (II) to the compound represented by Formula (I) may range from 1.5 to 3, preferably about 2.

In Formulas (I) and (II), all of $R_1$ to $R_4$ may be hydrogen. Specifically, the compound represented by Formula (I) may be a compound represented by Formula (III):

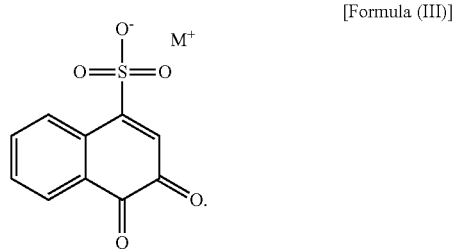

[Formula (III)]

In Formula (III), M may be the same as defined above.

Furthermore, the compound represented by Formula (II) may be a compound represented by Formula (IV):

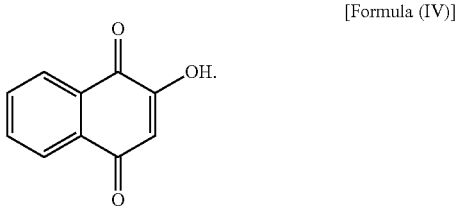 [SMILES: O=C1C=C(O)C(=O)c2ccccc21]

[Formula (IV)]

That is, the compound represented by Formula (II) may be Lawsone. Lawsone is known as an electrode active material, but has a problem in that its solubility in water is low so that the electrode capacity is also low. However, according to the present disclosure, when the compound represented by Formula (III), which is a precursor material of Lawsone, is included together in the electrolyte, the total solubility may increase, which may allow to provide an active material having a high electrode capacity.

The electrolyte according to the present disclosure may be a basic aqueous solution. Specifically, the electrolyte may be an aqueous solution containing a basic substance providing hydroxide ions, and may preferably contain KOH.

When the electrolyte having such a basic condition is used, hydroxide ions dissolved in water may be provided, and these hydroxide ions may be very important in the present disclosure. For example, when the compound represented by Formula (I) is a compound represented by Formula (III), and the compound represented by Formula (II) is a compound represented by Formula (IV) (i.e., Lawsone), a reaction in which the compound represented by Formula (III) reacts with a hydroxide ion to form the compound represented by Formula (IV) may be represented as shown in Scheme 1 below:

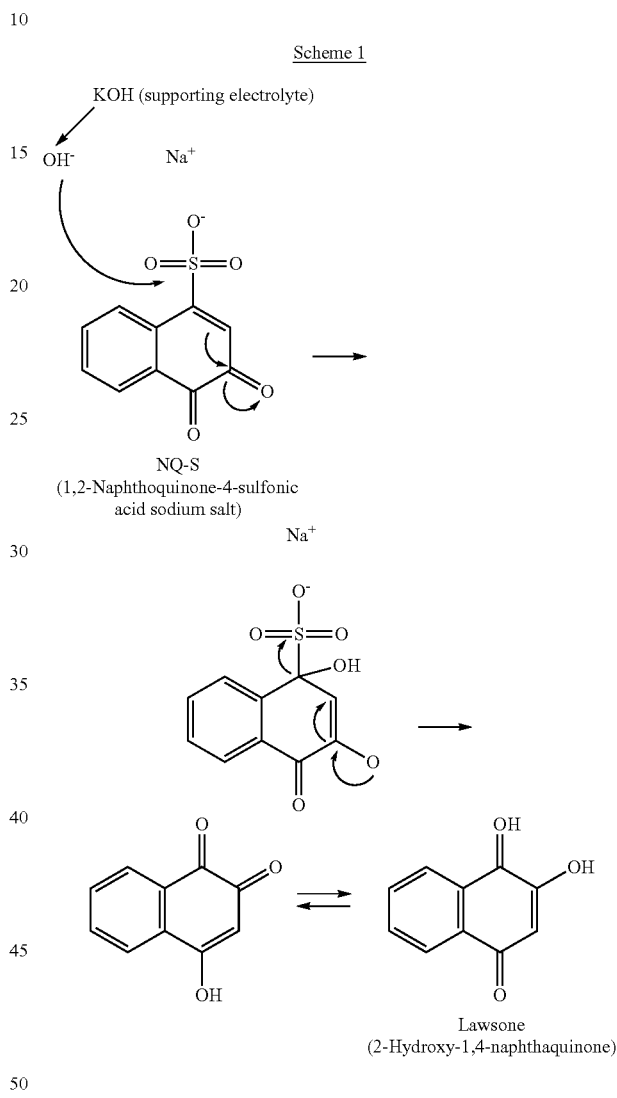

Although Scheme 1 has been shown for the compounds represented by Formulas (III) and (IV), it is possible to convert the compounds represented by Formula (I) having different substituents of $R_1$ to $R_4$ to a corresponding compound represented by Formula (II) through the same reaction. This is because $R_1$ to $R_4$ do not participate in the conversion reaction.

Therefore, when the compound represented by Formula (I) is included together with the compound represented by Formula (II), a relatively high solubility may be provided in comparison to when the compound represented by Formula (II) is included alone. The compound represented by Formula (II) may be additionally supplied by the conversion reaction and a sulfoxide ion released from the reaction may increase the solubility, and thus it is possible to provide an active material composition having a higher solubility.

A combined concentration of the compounds represented by Formulas (I) and (II) may be included in a concentration of 0.01 to 3 M, 0.05 to 2 M, 0.1 to 1.5 M, 0.2 to 1 M, 0.5 to 0.8 M, or about 0.6 M.

An aqueous solvent contained in an aqueous electrolyte may be water or a mixture of water and a hydrophilic solvent. Here, the hydrophilic solvent may include at least one selected from a group consisting of methanol, ethanol, n-propanol, isopropyl alcohol, n-butanol, t-butanol, ethylene glycol, and diethylene glycol.

The electrolyte may include an additional electrolyte in addition to the compounds represented by Formulas (I) and (II), and a solvent. The additional electrolyte may include at least one additional metal salt selected from $H_2SO_4$, $Li_2SO_4$, $Na_2SO_4$, $K_2SO_4$, LiCl, KOH, KCl, $H_3PO_4$, $HNO_3$, and any combination thereof. The above additional metal salt may be present in the electrolyte at a concentration of 0.05 M to 3 M, specifically 0.1 M to 2 M, and more specifically 0.1 M to 1.5 M.

An ARFB including the electrolyte according to the present disclosure may include the electrolyte according to the present disclosure as either a positive electrode electrolyte or a negative electrode electrolyte. In an embodiment, when the electrolyte according to the present disclosure is a positive electrode electrolyte, the negative electrode electrolyte may include a material that can be used as a negative active material of a redox flow battery (RFB) without a limitation. In another embodiment, when the electrolyte according to the present disclosure is a negative electrode electrolyte, the positive electrode electrolyte may be used as a positive active material for a RFB without a limitation. In an example embodiment, ferrocyanide was used as a negative active material, and the electrolyte according to the present disclosure was used as a positive active material, to confirm electrode activity. The ferrocyanide may be present in the electrolyte at a concentration of 0.05 M to 3.0 M, specifically 0.05 M to 2 M, more specifically 0.1 M to 1.5 M.

The battery may further include a positive electrode, a negative electrode, and a separator positioned between the positive electrode and the negative electrode. In addition, the battery may include a positive electrode electrolyte reservoir, a negative electrode electrolyte reservoir, and pumps. The positive electrode electrolyte reservoir and the negative electrode electrolyte reservoir may accommodate a positive electrode electrolyte and a negative electrode electrolyte, respectively. The pumps may pump the positive electrode electrolyte and the negative electrode electrolyte.

As the separator, an ion exchange membrane used in a conventional RFB may be used without a limitation, and may be, for example, a fluorine-based polymer, a partially fluorine-based polymer, or a hydrocarbon-based polymer, and may be specifically selected from a homo copolymer, an alternating copolymer, a random copolymer, a block copolymer, a multiblock copolymer, and a grafting copolymer of one or at least two polymers selected from a group consisting of perfluorosulfonic acid-based polymers, hydrocarbon-based polymers, aromatic sulfone-based polymers, aromatic ketone-based polymers, polybenzimidazole-based polymers, polystyrene-based polymers, polyester-based polymers, polyimide-based polymers, polyvinylidene fluoride-based polymers, polyethersulfone-based polymers, polyphenylene sulfide-based polymers, polyphenylene oxide-based polymers, polyphosphazene-based polymers, polyethylene naphthalate-based polymers, polyester-based polymers, doped polybenzimidazole-based polymers, polyetherketone-based polymers, polyphenylquinoxaline-based polymers, polysulfone-based polymers, sulfonated polyarylene ether-based polymers, sulfonated polyetherketone-based polymers, sulfonated polyetheretherketone-based polymers, sulfonated polyamide-based polymers, sulfonated polyimide-based polymers, sulfonated polyphosphazene-based polymers, sulfonated polystyrene-based polymers and radiation-polymerized sulfonated low-density polyethylene-g-polystyrene-based polymers. The separator may be an anion exchange membrane or a porous membrane.

A positive electrode and a negative electrode of the present disclosure may be each independently at least one selected from a group consisting of gold (Au), tin (Sn), titanium (Ti) platinum (Pt), platinum-titanium (Pt—Ti), iridium oxide-titanium (IrO—Ti), and carbon. The electrode should have excellent electrical conductivity and mechanical strength, and need to be chemically and electrochemically stable. In addition, when the electrode is applied to a battery, the electrode may need to show a high efficiency, be inexpensive, and need to be a material in which oxidation/reduction reactions with an active material occur reversibly. In consideration of such criteria, as described above, at least one selected from a group consisting of gold (Au), tin (Sn), titanium (Ti), platinum-titanium (Pt—Ti), iridium oxide-titanium (IrO—Ti), and carbon materials may be used as an electrode, and other materials that satisfy the above criteria and maintain stability in acidic electrolyte or basic electrolyte may be used as an electrode. The carbon material has advantages of inexpensive price, high chemical resistance in acidic and basic electrolytes, and easy surface treatment. In particular, among carbon materials, carbon felt is advantageous in that it has chemical resistance, stability in a wide voltage range, and high strength characteristics. However, when an electrode is manufactured only with carbon and graphite, the electrode may be fragile. To overcome such an issue, the carbon polymer composite electrode obtained by mixing a binder such as polyvinylidene (PVDF), high density polyethylene (HDPE), polyvinyl acetate (PVA) and polyolefine with a conductive material such as carbon black and graphite fibers may be used. In an example, a glassy carbon electrode (GCE) electrode was used.

According to example embodiments, an electrolyte according to the present disclosure may achieve superior solubility of an electrode active material to the conventional electrolytes containing only a hydroxynaphthoquinone compound. Thus, it is possible to achieve a higher capacity.

BRIEF DESCRIPTION OF THE SEVERAL VIEWS OF THE DRAWING(S)

These and/or other aspects, features, and advantages of the invention will become apparent and more readily appreciated from the following description of example embodiments, taken in conjunction with the accompanying drawings of which:

FIG. 1 schematically illustrates principles of the present disclosure;

FIGS. 2A, 2B and 2C illustrate CV curves, absorbance curves, and reaction mechanism of NQ-S, NQ-OH, and the like, confirmed in Experimental Example 1; and specifically, FIG. 2A illustrates CV curves for each of the NQ-S immediately after and at 2 hours, 4 hours, 6 hours after addition to a KOH aqueous solution, and NQ-OH alone solution, FIG. 2B illustrates absorbance curves for each of the NQ-S immediately after and at 6 hours after addition to the KOH aqueous solution, and NQ-OH alone solution, and FIG. 2C illustrates a reaction process of NQ-S to NQ-OH in the KOH solution;

FIG. 3A illustrates an absorbance versus a concentration of a Lawsone alone solution, FIG. 3B illustrates absorbance curves of Lawsone, NQ-S and NQ-SO, and FIG. 3C illustrates an interaction between NQ-SO and KOH;

FIG. 5A illustrates their CV curves, and FIG. 5B illustrates their resistance values, and FIG. 5C illustrates their absorbance values;

FIG. 6A illustrates a redox reaction of Lawsone, FIG. 6B illustrates a redox reaction of ferrocyanide, and FIG. 6C illustrates the CV curves of each of Lawsone and ferrocyanide relative to Ag/AgCl;

FIG. 8A illustrates a charge-discharge curve in a first cycle, FIG. 8B illustrates charge-discharge curves during cycling, FIG. 8C illustrates a charging efficiency during cycling, and FIG. 8D illustrates a state of charge (SOC) % and a discharge capacity during cycling;

FIG. 9A illustrates CV curves of Lawsone relative to Ag/AgCl, and FIG. 9B illustrates CV curves of ferrocyanide relative to Ag/AgCl;

Figure 11A:
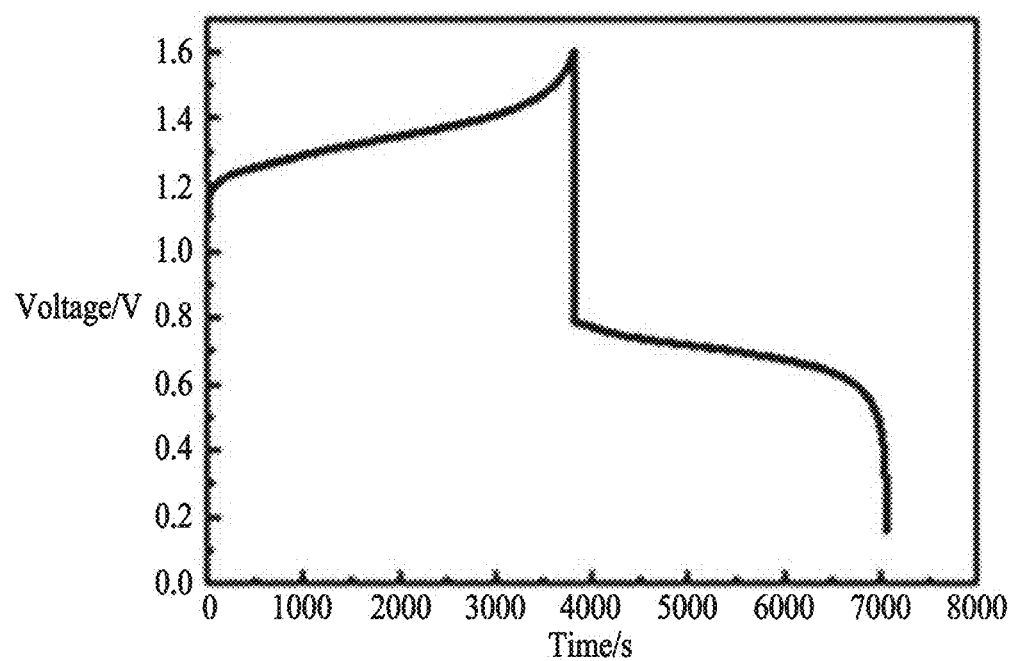
Figure 11B:
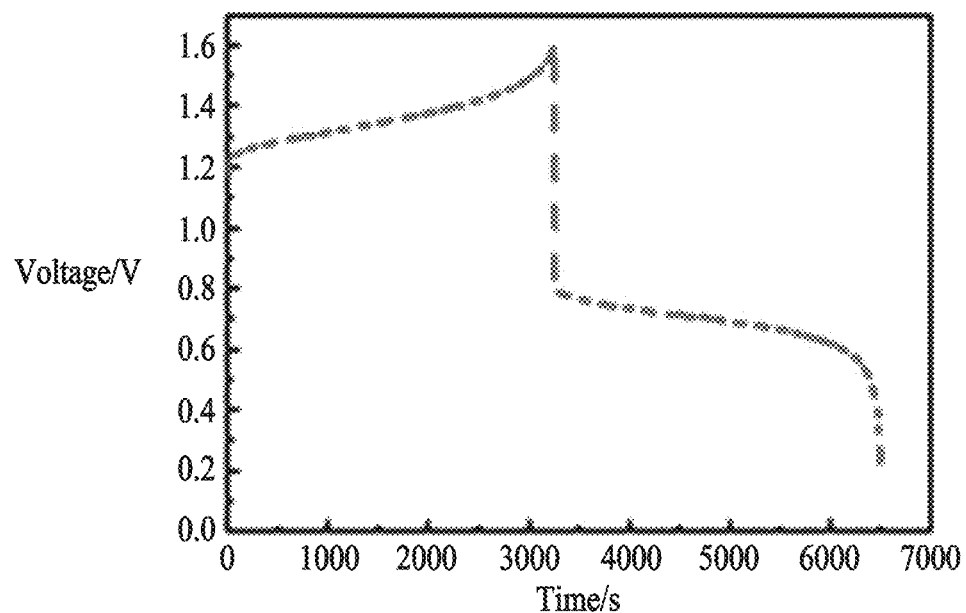
Figure 11C:
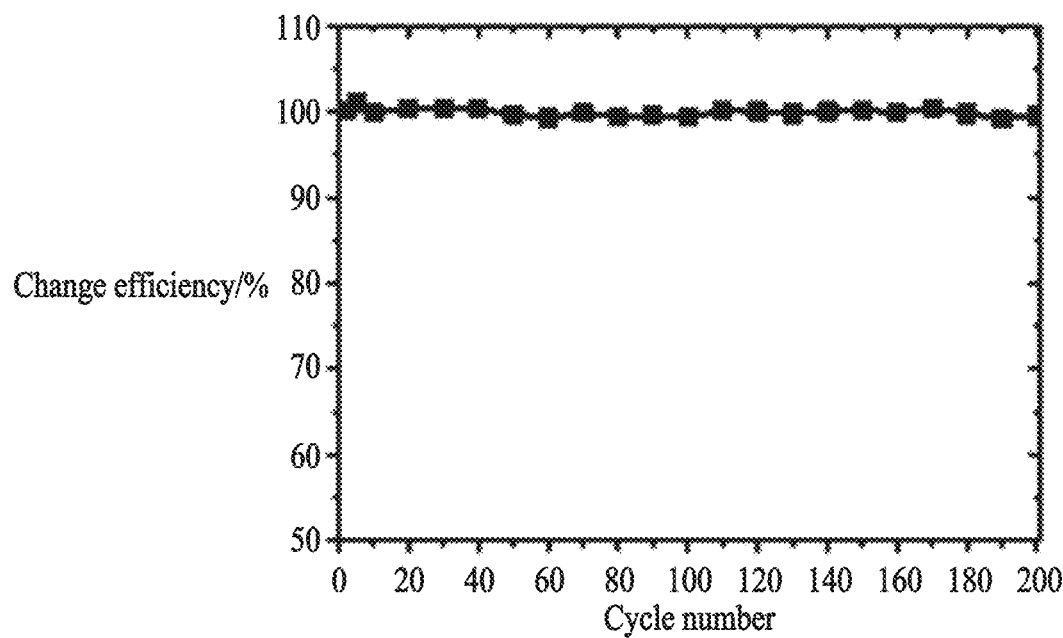
Figure 11D:
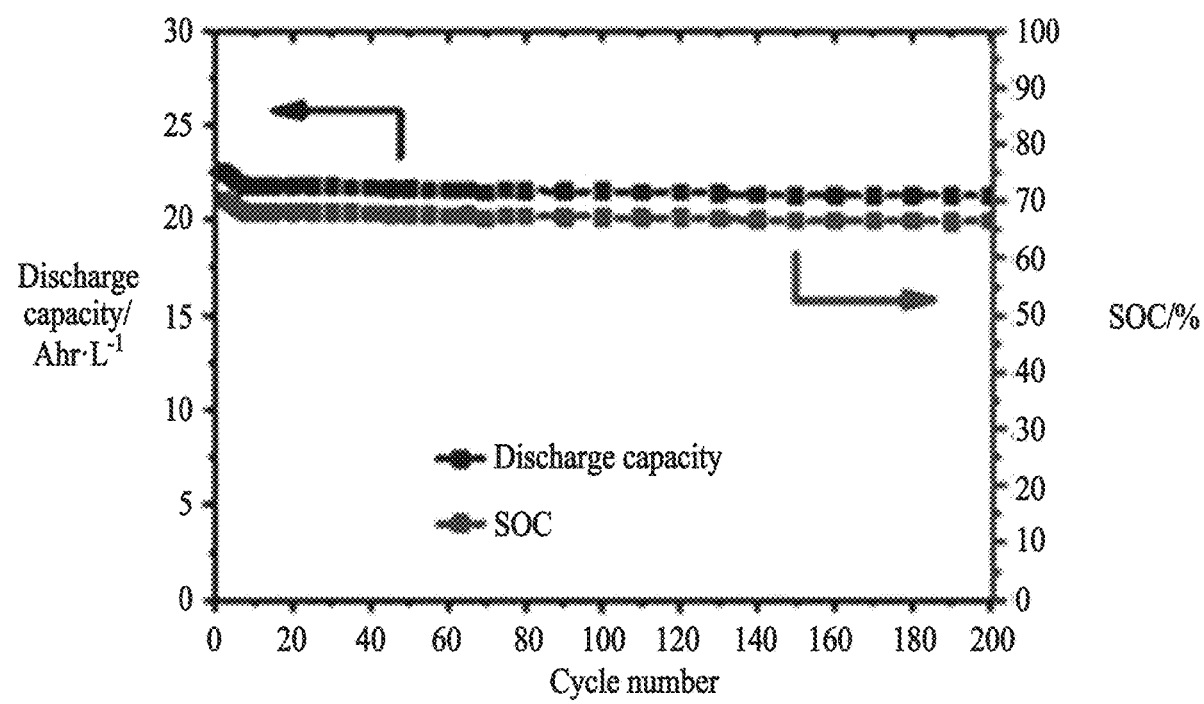
Figure 12A:
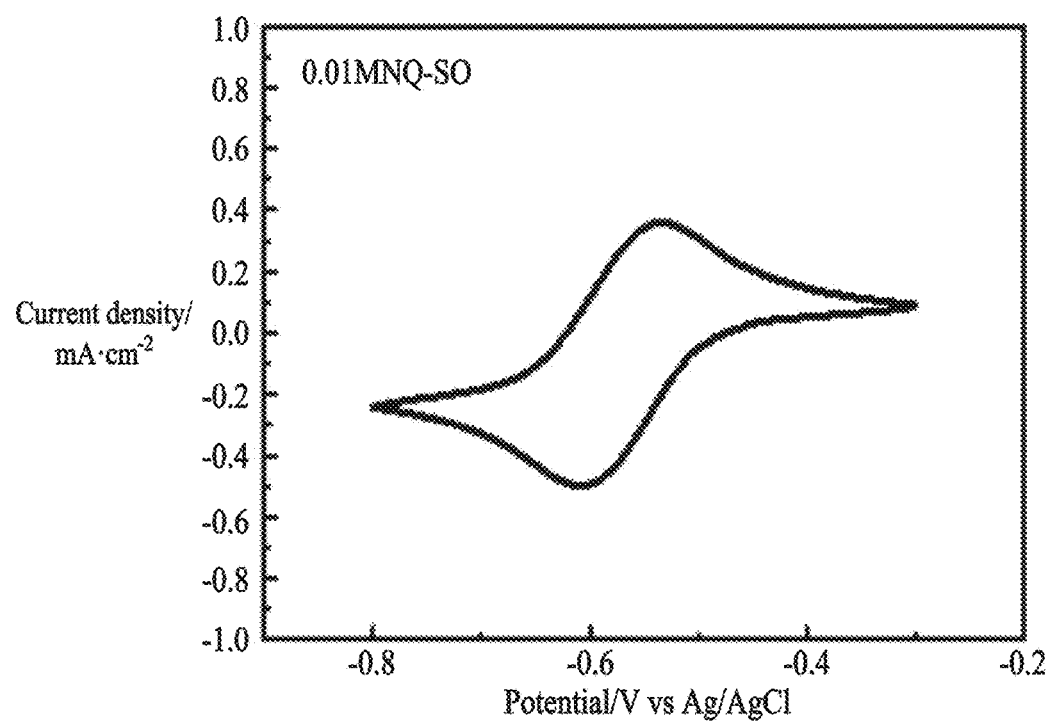
Figure 12B:
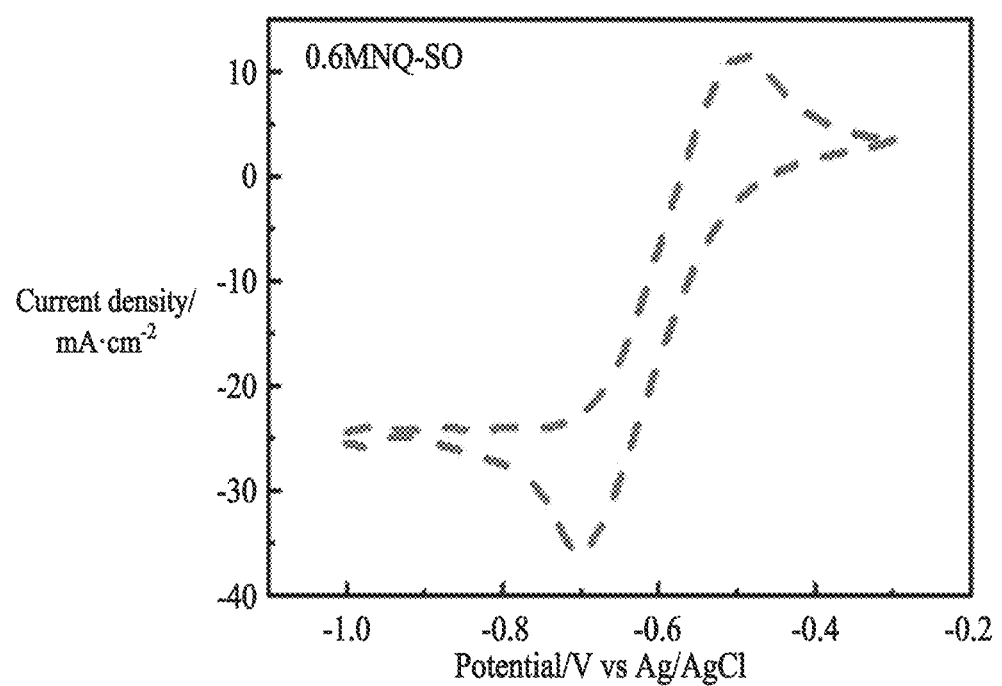

FIGS. 11A, 11B, 11C and 11D illustrate electrode performance of a full cell using a 0.6M NQ-SO solution confirmed in Experimental Example 5; and FIG. 11A illustrates a charge-discharge curve in a first cycle, FIG. 11B illustrates a charge-discharge curve in a second cycle, FIG. 11C illustrates a charging efficiency as a function of cycling number, and FIG. 11D illustrates an SOC % and a discharge capacity as a function of cycling number; and FIGS. 12A and 12B illustrate CV curves of an NQ-SO solution confirmed in Experimental Example 5.

DESCRIPTION OF SPECIFIC EMBODIMENTS OF THE INVENTION

Hereinafter, example embodiments will be described in detail with reference to the accompanying drawings. However, as various changes may be applied to the example embodiments, the right scope of patent application is not restricted or limited by the example embodiments. It should be understood that all modifications, equivalences, or substitutions for the example embodiments are included in the right scope.

Terms used in the example embodiments are used for the purposes of illustration only, but should not be interpreted as intended to limit the example embodiments. An expression used in the singular encompasses the expression in the plural, unless it has a clearly different meaning in the context. In this specification, it should be understood that a term such as "comprises" or "having" is used to specify the presence of features, numbers, steps, operations, constituent elements, parts, or any combination thereof described in the specification, but it does not preclude the possibility of the presence or addition of one or more other features, numbers, steps, operations, constituent elements, parts, or any combination thereof.

Unless otherwise defined, all terms (including technical and scientific terms) used herein have the same meaning as commonly understood by one of ordinary skill in the art to which the example embodiments belong. It will be further understood that terms, such as those defined in commonly used dictionaries, should be interpreted as having a meaning that is consistent with their meaning in the context of the relevant art and will not be interpreted in an idealized or overly formal sense unless clearly defined in the present application.

In describing the example embodiments with reference to the accompanying drawings, like elements will be referenced by like reference numerals or signs regardless of the drawing numbers, and description thereof will not be repeated. In describing the example embodiments, when it is determined that a detailed description of well-known technology relating to the present disclosure unnecessarily makes the gist of the example embodiments obscure, the detailed description thereof will be omitted.

Throughout this specification, "%" used to indicate a concentration of a particular substance means (weight/weight) % for solid/solid, (weight/volume) % for solid/liquid, and (volume/volume) % for liquid/liquid, unless otherwise noted.

Used Materials 1,2-naphthoquinone-4-sulfonic acid sodium salt (NQ-S), 2-hydroxy-1,4-naphthoquinone (Lawsone), and FeCN were purchased from Alfa Aesar, and KCl and KOH were purchased from Samchun Chemical.

Experimental Example 1. Analysis of Reaction of NQ-S to NQ-OH Compound

Conversion of NQ-S to NQ-OH was observed through the following processes.

Initially, 0.01 M NQ-S was dissolved in 1 M KOH and then the NQ-S solution was stayed for few hours. Changes in a chemical structure of the NQ-S solution were observed using cyclic voltammetry and UV-vis spectroscopy.

Figure 1:
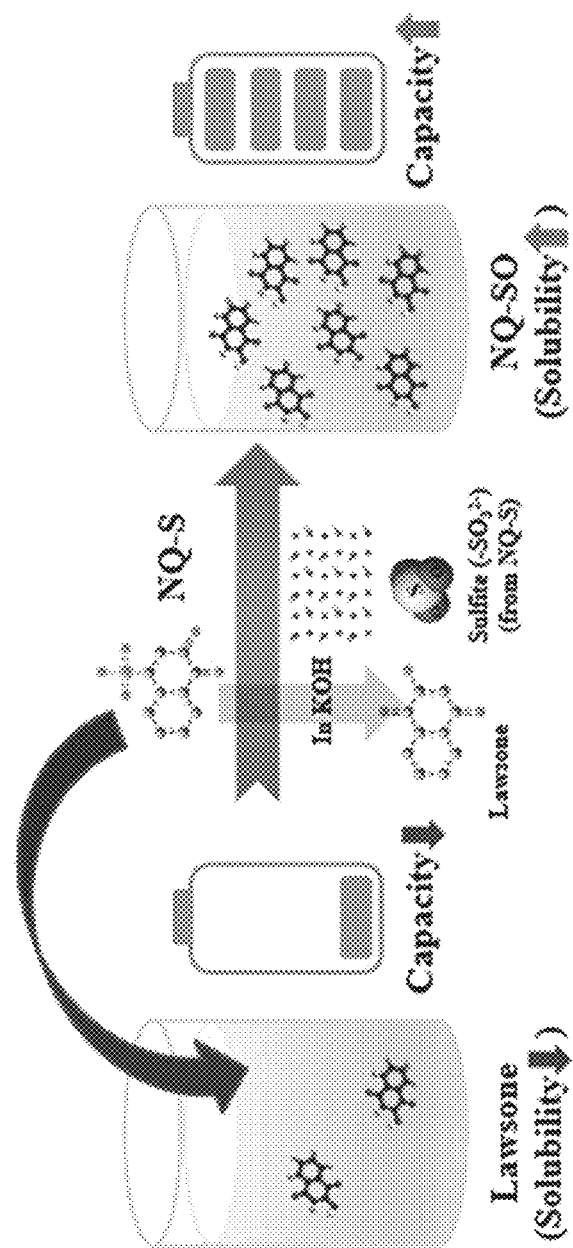
Figure 2A:
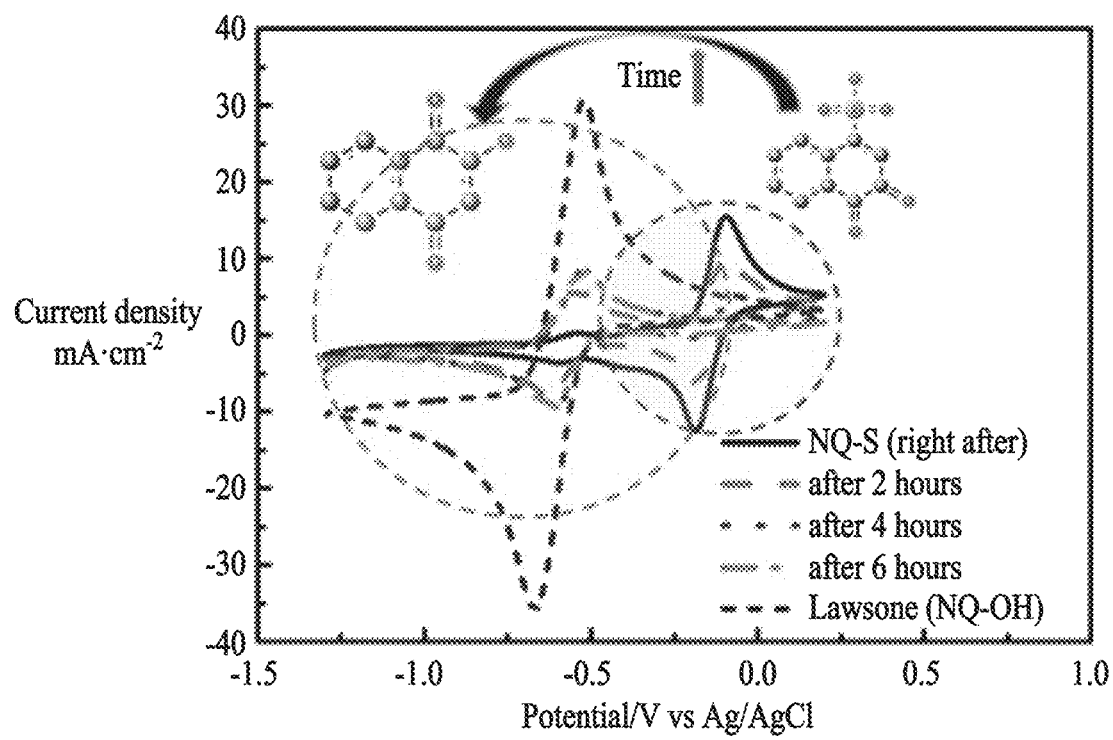

According to the CV curves shown in FIG. 2A, a redox potential of −0.1 V vs Ag/AgCl was observed when NQ-S was observed right after a dissolution of NQ-S into a KOH solution. On the other hand, another redox potential (−0.55 V vs Ag/AgCl) was observed when the NQ-S dissolved in the KOH solution was stayed for 2 hours. It may be found that a redox reaction peak that was observed at −0.55 V vs Ag/AgCl corresponds to that of Lawsone (natural NQ-OH form), which indicates that NQ-S got more and more transformed into NQ-OH over time.

When the staying time was extended into 6 hours, only the redox potential peak of −0.55 V vs Ag/AgCl was observed, which may indicate that the NQ-S was completely transformed into NQ-OH.

Figure 2B:
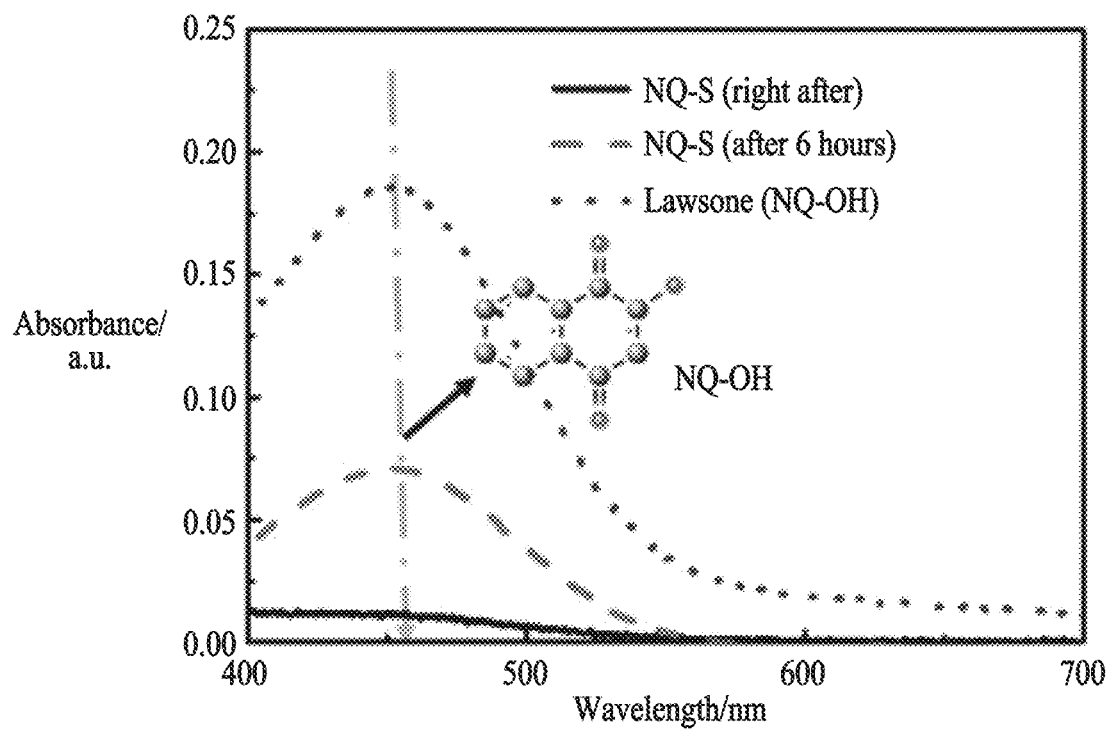

For the UV-vis spectroscopy, the following three samples were prepared: (i) NQ-S that is just dissolved in KOH (sample 1); (ii) NQ-S dissolved in KOH for 6 hours (sample 2); and (iii) pristine Lawsone (sample 3). In FIG. 2B, a peak observed at 455 nm corresponds to a peak for NQ-OH, and the peak was clearly observed in sample 2. In other words, it may be found that the NQ-S was completely transformed into NQ-OH after six hours.

Figure 2C:
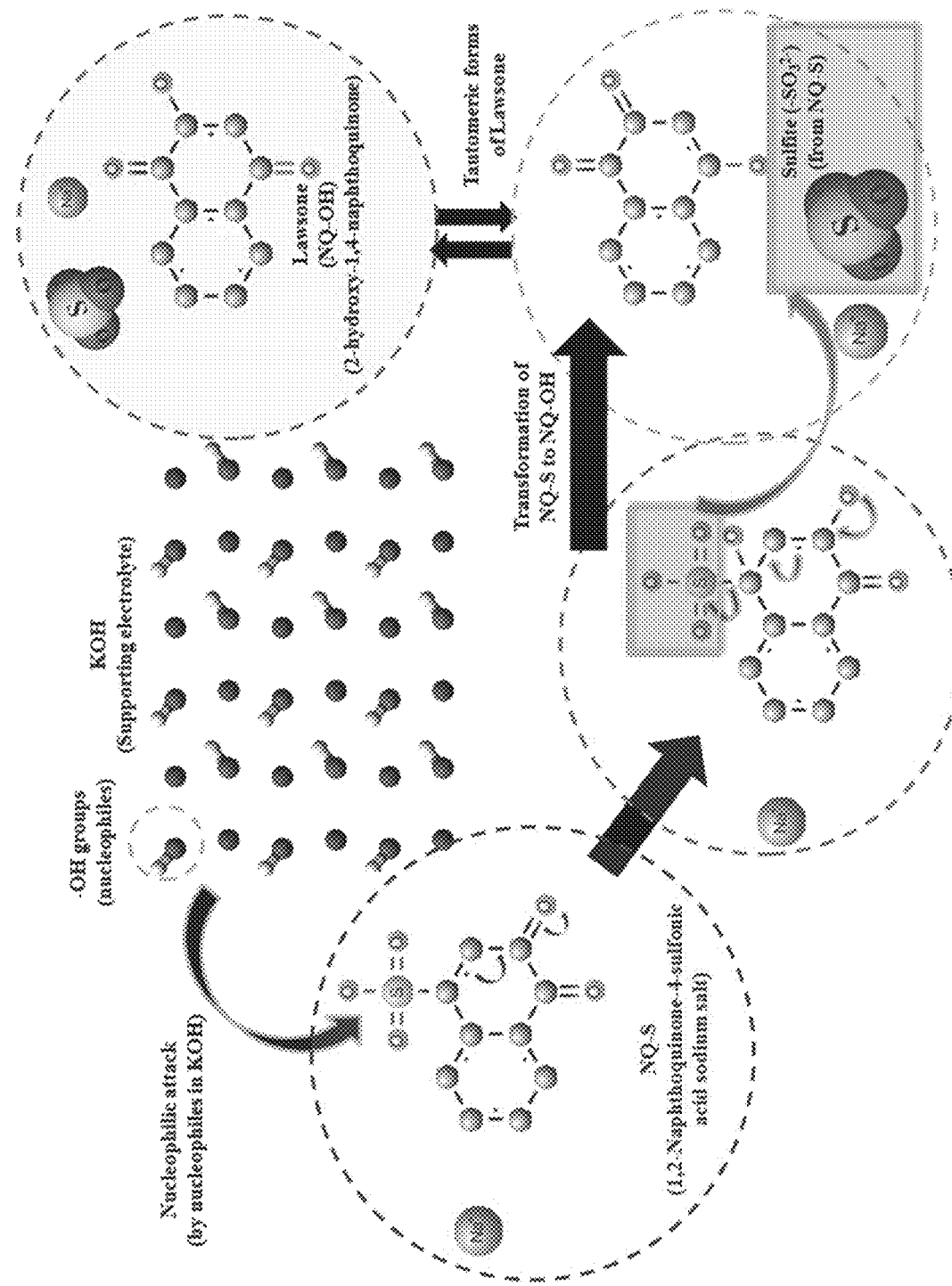

The above conversion mechanism from NQ-S to NQ-OH is illustrated in FIG. 2C.

Experimental Example 2: Solubility Analysis

Excessive amounts of solutions of NQ derivatives were prepared. (i) Lawsone alone, (ii) NQ-S alone, and (iii) a mixture (hereinafter, referred to as "NQ-SO") of NQ-S and Lawsone were dissolved in a 1 M KOH solution and stirred for 24 hours. When a further period of time elapsed after stirring was stopped, each solution was divided into two parts (upper and lower parts). 400 microliters (L) of the upper part of the solution was collected and observed by a UV-vis spectrometer. An absorbance was measured to determine concentrations of NQ derivatives.

Figure 3A:
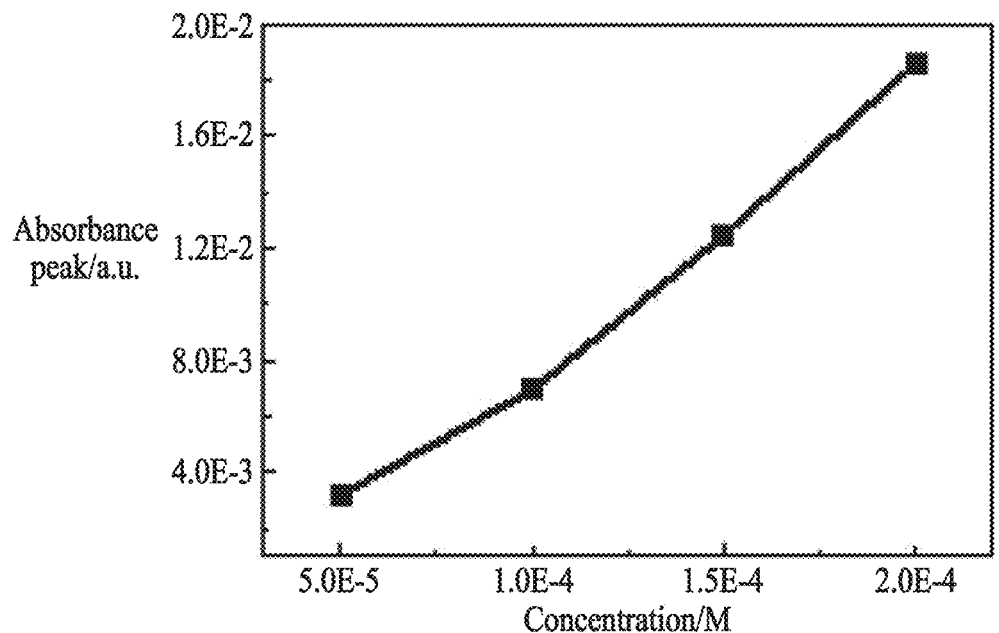
FIGS. 3A, 3B and 3C illustrate solubility of NQ derivates confirmed in Experimental Example 2; and specifically.

As a control group, a solution with a known concentration of Lawsone was prepared, and UV-vis spectroscopy of the solution was measured. When absorbance peaks of the control group and a sample of NQ derivatives were compared, concentrations of the samples were calibrated and calculated. An absorbance based on a known concentration of pristine Lawsone used as the control group is shown in FIG. 3A.

Figure 3B:
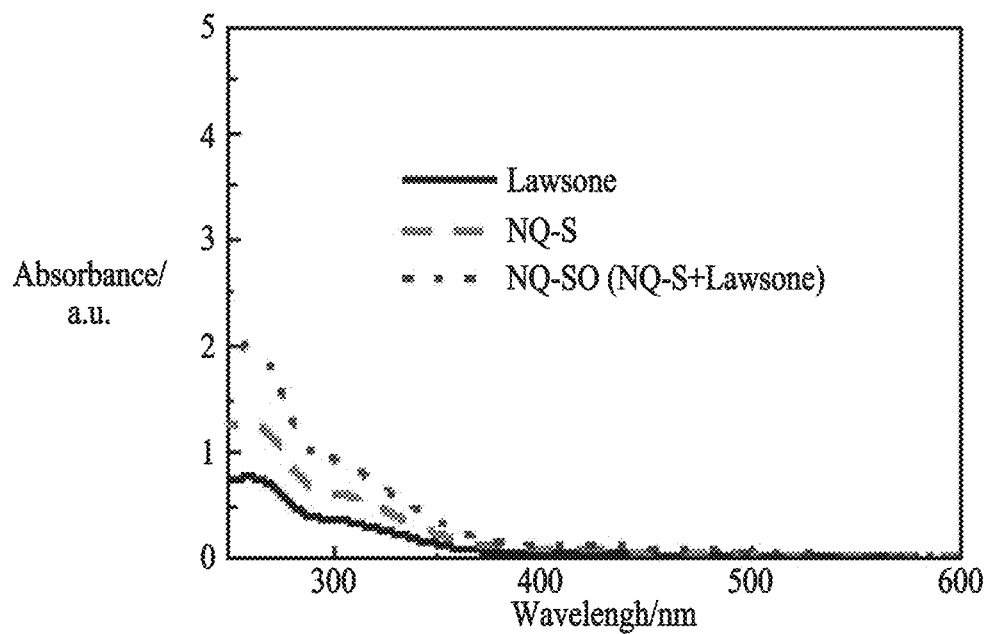

Since a solubility of NQ-S (0.83 M) in a KOH solution is higher than that of Lawsone (0.42 M) in a KOH solution, when NQ-S is mixed with Lawsone, it was expected that a solubility of the mixture after transformation of NQ-S may be higher than that of Lawsone. Absorbance peaks of Lawsone, NQ-S and NQ-SO were actually measured by UV-vis spectroscopy and shown in FIG. 3B. The NQ-SO has the sharpest spectrum, which indicates that the solubility of NQ-SO is highest. Actually, when a molar ratio of NQ-S and Lawsone was 1:2, a calculated maximum soluble concentration of NQ-SO in KOH was 1.26 M, and the above concentration was much higher than a concentration of Lawsone alone and a concentration of NQ-S alone. The concentration of the Lawsone alone was 0.42 M, and the concentration of the NQ-S alone was 0.83 M, as shown in FIG. 3B.

There are two possible reasons for this.

First, a sulfite ($-SO_3^{2-}$) group released by transformation of NQ-S may be a hydrophilic functional group and may act as an additive for increasing the solubility of Lawsone. Therefore, it is possible to increase the solubility of Lawsone having naturally low solubility in an aqueous solution.

Figure 3C:
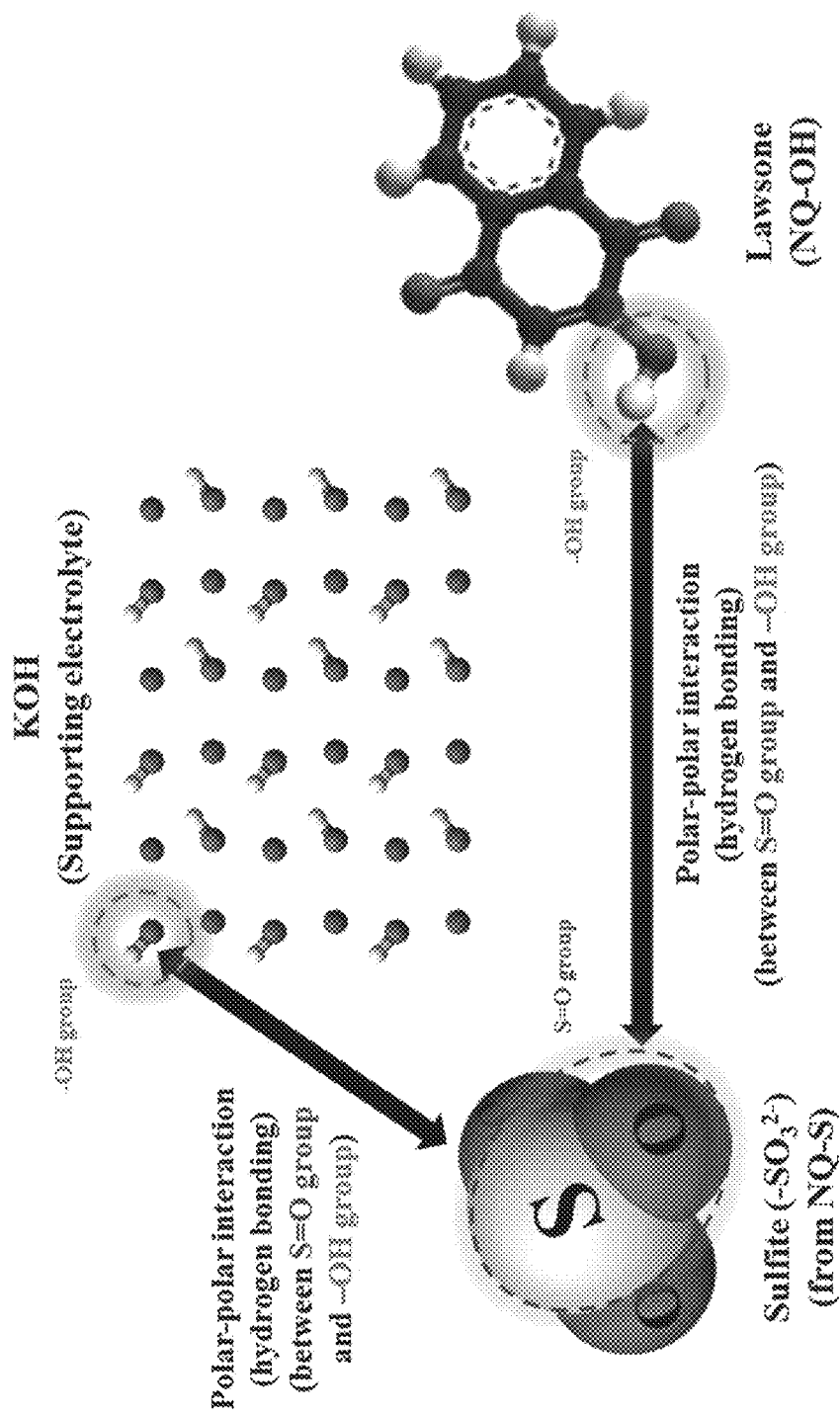

Second, two polar-polar interactions (i) between an S=O group of $-SO_3^{2-}$ and an —OH or C=O group of Lawsone or NQ-OH transformed from NQ-S and (ii) between the S=O group of $-SO_3^{2-}$ and —OH groups of a KOH electrolyte may occur. The interactions may strengthen a connection between NQ-SO and KOH electrolyte, to increase its solubility in an aqueous solution, as shown in FIG. 3C.

Figure 4:
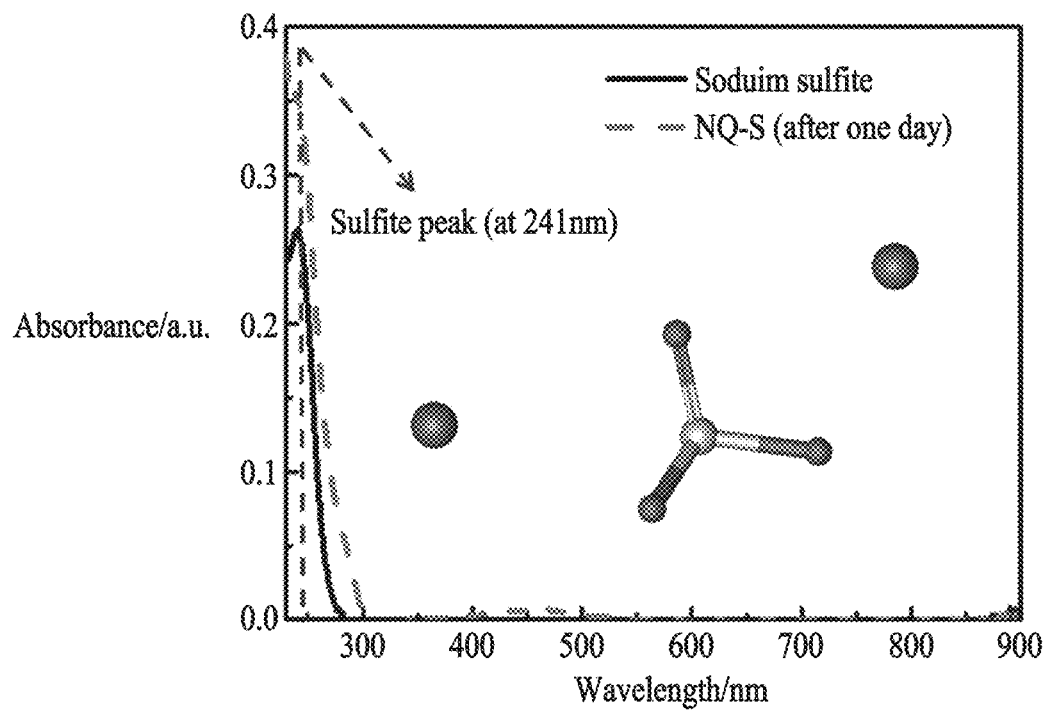
FIG. 4 illustrates absorbance values of each of an NQ-S solution and a sodium sulfite solution confirmed in Experimental Example 2.

Also, a reaction of the $-SO_3^{2-}$ group within an NQ-S dissolved in the KOH solution was observed by the UV-vis spectroscopy. Specifically, to identify the $-SO_3^{2-}$ within the NQ-S solution, the NQ-S dissolved in the KOH solution was stayed for 24 hours and its UV-vis spectroscopy was measured, as shown in FIG. 4. For a comparison, a 1 M aqueous solution of potassium sulfite ($K_2SO_3$) was prepared and its UV-vis spectroscopy was also shown in FIG. 4.

According to FIG. 4, the $-SO_3^{2-}$ peak was observed at 241 nm even after the NQ-S solution was stayed for 24 hours, which indicates that the $-SO_3^{2-}$ was released from the NQ-S solution over time.

Experimental Example 3. Analysis of Ratio of Lawsone and NQ-S

How a ratio of Lawsone and NQ-S has an influence on a redox reaction is confirmed as follows.

Samples of Lawsone and NQ-S having different ratios were prepared, and a resistance and a solubility of samples were measured electrochemically (by cyclic voltammetry (CV) and electrochemical impedance spectroscopy (EIS)) and optically (by UV-vis spectroscopy).

Specifically, the following five samples were prepared: (i) a 1:1 ratio of NQ-S and Lawsone (0.15 M NQ-S:0.15 M Lawsone); (ii) a 1:2 ratio of NQ-S and Lawsone (0.1 M NQ-S:0.2 M Lawsone); (iii) a 2:1 ratio of NQ-S and Lawsone (0.2 M NQ-S:0.1 M Lawsone); (iv) only Lawsone (0.3 M Lawsone); and (v) only NQ-S (0.3 M NQ-S).

Figure 5A:
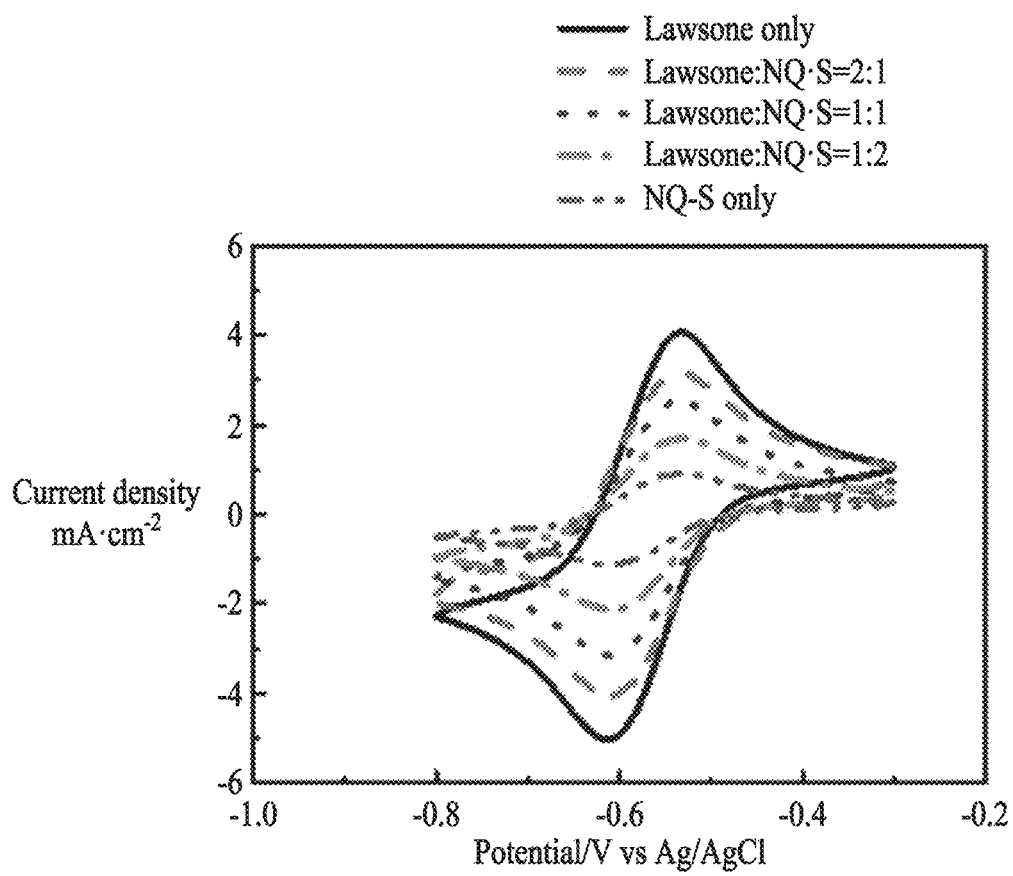
FIGS. 5A, 5B and 5C illustrate an observation of samples having different ratios of Lawsone and NQ-S confirmed in Experimental Example 3.

CV curve measurement results of the five samples were shown in FIG. 5A. A redox reactivity was proportional to a proportion of Lawsone. This is related to a transformation process of NQ-S. When NQ-S is transformed, both undesirable by-products and desirable NQ-OH may be generated. Here, the desirable NQ-OH that has the same chemical structure as that of Lawsone has an excellent redox reactivity, while the undesirable by-products may not have an appropriate redox reactivity. Thus, the redox reactivity may depend on the proportion of Lawsone.

Referring to FIG. 5A, when 0.1 M NQ-S is dissolved in 1 M KOH, one third of NQ-S is transformed to desirable NQ-OH (0.033 M), and the $-SO_3^{2-}$ released by the transformation allows the solubility of NQ-OH to increase, and accordingly a solubility of a mixture of NQ-S and Lawsone in KOH also increases.

Figure 5B:
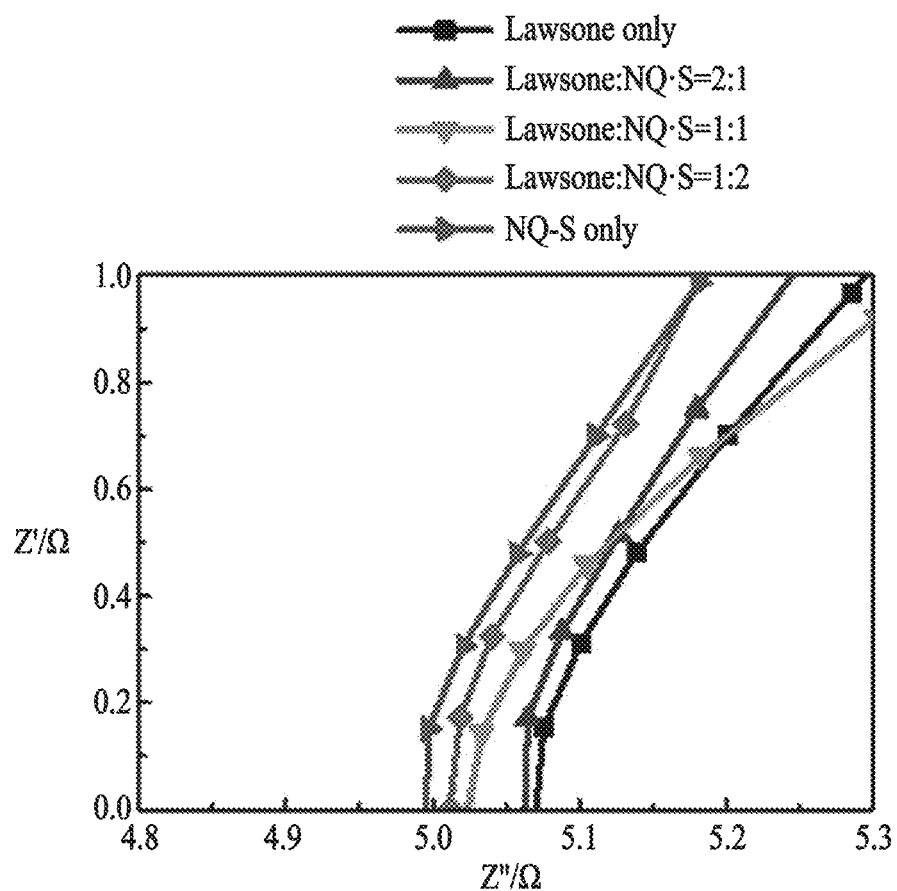
Figure 5C:
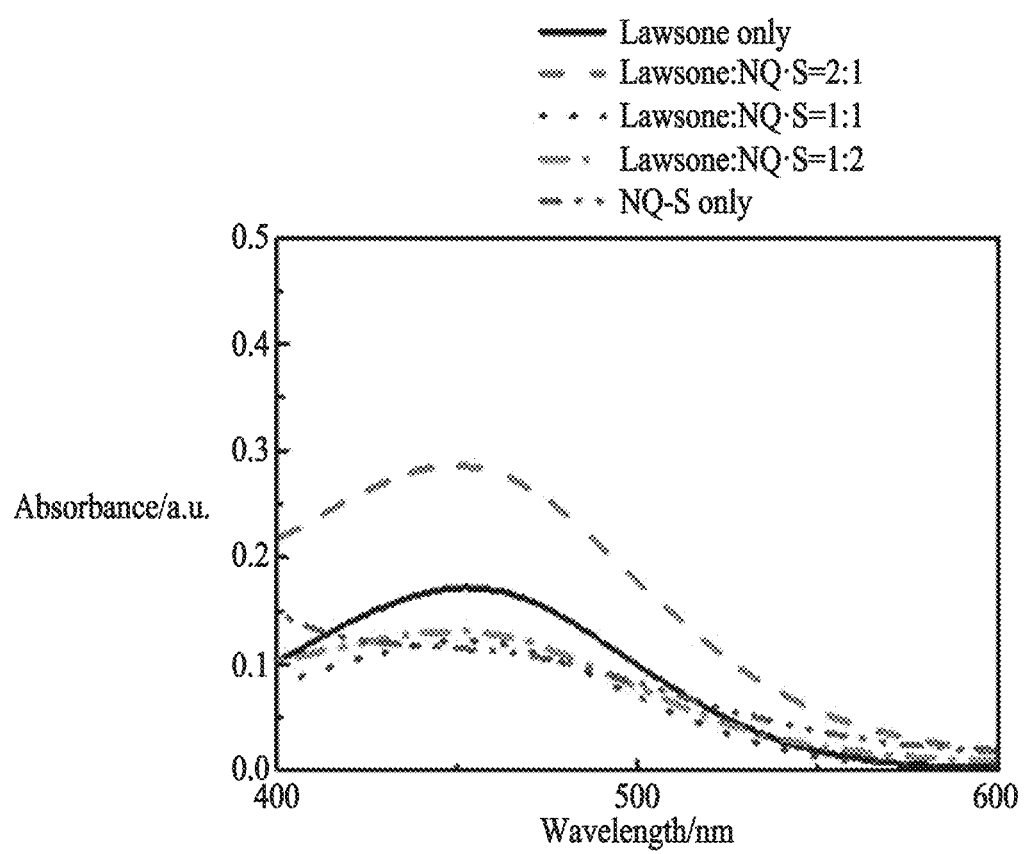

An ohmic resistance that is measured by EIS decreases, as a proportion of NQ-S increases, as shown in FIG. 5B. Ohmic resistances of the samples was 4.99 Q (only NQ-S), 5.01 (2 (a 2:1 ratio of NQ-S to Lawsone), 5.03 Q (a 1:1 ratio of NQ-S to Lawsone), 5.06 Q (a 1:2 ratio of NQ-S to Lawsone) and 5.07 (2 (only Lawsone). This is also due to the $SO_3^{2-}$. The $SO_3^{2-}$ has a hydrophilic property, and lowers a viscosity and resistance of electrolyte. In FIGS. 5A and 5B, it may be found that the redox reactivity is proportional to the proportion of Lawsone, and that the ohmic resistance is proportional to the proportion of NQ-S. Thus, an optimal ratio may be determined by a solubility in KOH. The solubility in KOH was measured by UV-vis spectroscopy, as shown in FIG. 5C. The highest solubility in KOH was observed as 1.26 M in a 2:1 ratio of Lawsone to NQ-S.

A maximum overall solubility of NQ-SO in KOH is strongly a☐ected by an amount of $-SO_3^{2-}$. When an appropriate amount of $-SO_3^{2-}$ is dissolved in KOH, $-SO_3^{2-}$ may act as a hydrophilic additive and may form a hydrogen bonding between KOH and NQ-SO. The $-SO_3^{2-}$ may also absorb water instead of Lawsone, to prevent a hydration of Lawsone in KOH. As a result, the solubility of Lawsone increases. In other words, since $-SO_3^{2-}$ is used as a hygroscopic additive, the solubility of Lawsone in KOH may increase and the overall solubility of NQ-SO may also increase. However, an excessive amount of $-SO_3^{2-}$ dissolved in KOH may negatively a☐ect the solubility of Lawsone. In other words, the $-SO_3^{2-}$ has a naturally weak alkaline property, and an excessive amount of the $-SO_3^{2-}$ may allow the KOH to become more alkaline. Accordingly, under the above state, Lawsone may be deprotonated and the deprotonated Lawsone may lower its solubility in KOH.

Experimental Example 4. Electrochemical Characterization Observation

To observe electrochemical performance of active species, various half-cell tests were performed as follows by using a computer connected potentiostat (SP-240, Bio-Logic).

Ag/AgCl (soaked in 3.0 M NaCl) and Pt wire were used as a reference electrode and a counter electrode, respectively. A glassy carbon electrode with an active area of 0.1936 cm$^2$ was used as a working electrode. CV curves of the related samples were also observed. 0.01 M of NQ derivatives (Lawsone, NQ-S, and NQ-SO) was dissolved in 1 M KOH to prepare a solution, and then CV curves of NQ derivatives were measured.

In the case of potassium ferrocyanide, 0.01 M of potassium ferrocyanide was dissolved in 1 M KOH or 1 M KCl to prepare a solution. Similarly, the half-cell test was performed and then CV curves of NQ derivatives were measured.

Figure 6A:
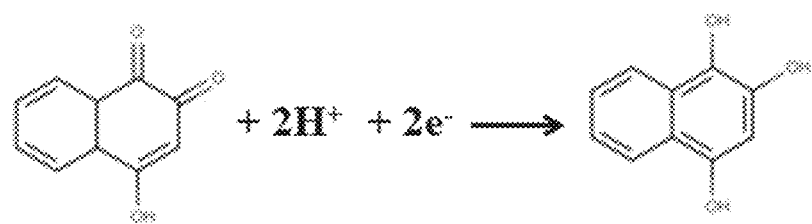
FIGS. 6A, 6B and 6C illustrate a redox reaction equation and CV curves for a half-cell of an electrode active material of each electrolyte confirmed in Experimental Example 4; and specifically.
Figure 6B:
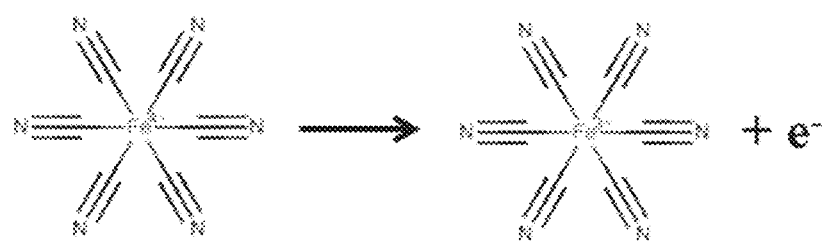
Figure 6C:
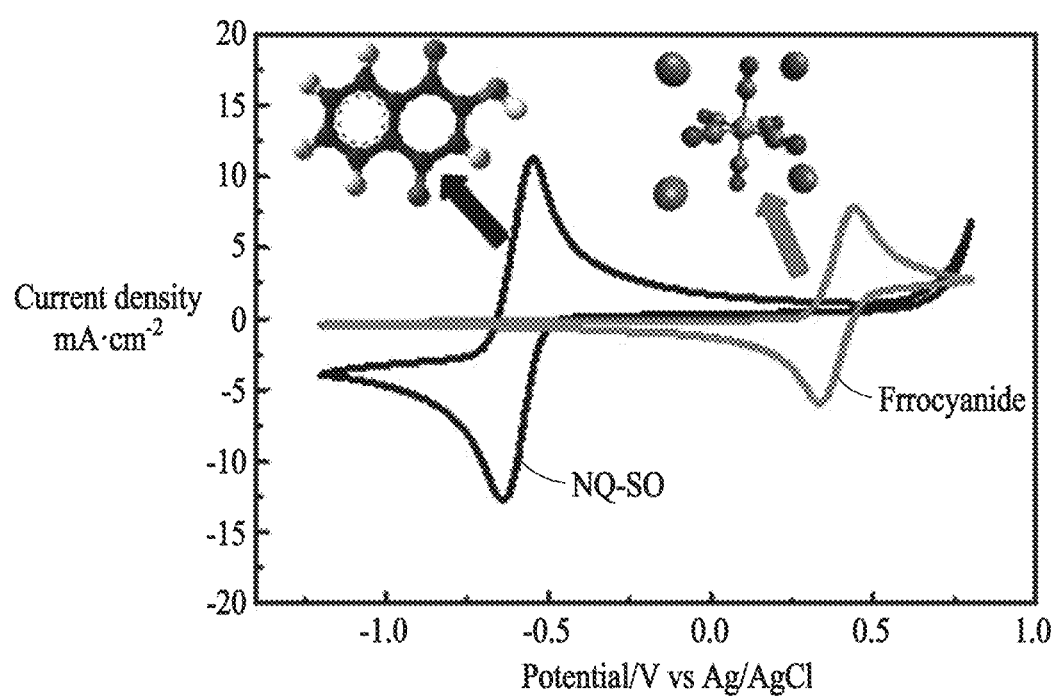

Redox reaction processes of NQ-SO and FeCN are shown in FIGS. 6A and 6B. A cell voltage of NQ-SO and FeCN in KOH electrolyte was measured as 1.01 V, as shown in FIG. 6C. To enhance performance of a RFB, performance of NQ derivatives, for example, Lawsone, NQ-S and NQ-SO, included in active materials needs to be optimized. To this end, kinetic parameters of NQ derivatives were measured and compared. To calculate electrochemical properties of NQ derivatives, the CV curves were used. To measure reaction kinetic parameters, such as an average redox potential separation value ΔEp,avg and a dilusion coeQcient D, CV curves were also observed at a scan rate range of 10 to 100 mV·s$^{-1}$. A value of D was measured by a Randles-Sevick's equation.

By a CV measurement, an average diuerence of anodic and cathodic redox potentials and a diﬀusion coeﬂcient which is related to an electron transfer rate, were calculated. In a redox potential diﬀerence, those of Lawsone, NQ-S and NQ-SO were similar as 0.077 V, which indicates that an electron transfer rate of NQ derivatives is not significantly diﬀerent. This is because their final forms are the same as NQ-OH. In contrast, their diﬀusion coeﬀcients were diﬀerent and dependent on the amount of Lawsone. As the amount of Lawsone increases, a redox reactivity increased and a diﬀiusion coeﬀcient of Lawsone ($1.75 \cdot 10^{-6}$ cm$^2 \cdot$s$^{-1}$) was higher than those of NQ-S ($4.62 \cdot 10^7$ cm$^2 \cdot$s$^{-1}$) and NQ-SO ($1.18 \cdot 10^{-6}$ cm$^2 \cdot$s$^{-1}$). In conclusion, the diﬀusion coeﬀcient of Lawsone is higher than that of NQ-SO containing NQ-S, because NQ-S is not transformed to Lawsone only, and NQ-S is also transformed into other forms. When only Lawsone is present, Lawsone may have the superior redox reactivity on the same concentration basis, and accordingly the superior diffusion coefficient. However, when only Lawsone is used, the solubility may be significantly reduced. Due to a low solubility of Lawsone, it is not suitable to use Lawsone as a sole active material for the RFB, despite a high reactivity. Therefore, though Lawsone is quite excellent in terms of a diffusion coefficient, NQ-S is also included together with Lawsone to increase the solubility.

Experimental Example 5. Electrochemical Performance Analysis on Aqueous Redox Flow Battery (ARFB)

Performance of an ARFB full cell was observed using charge-discharge equipment (Wonatech, WBCS3000). A catholyte was prepared by dissolving 0.4 M potassium ferrocyanide (FeCN) into 1 M KOH (60 mL). An anolyte was prepared by dissolving 0.2 M NQ-S and 0.4 M Lawsone into 20 mL of KOH (0.6 M NQ-SO in 1 M KOH). Carbon felt (made by Toyobo) and Nafion 117 were used as an electrode and a separator, respectively.

Figure 7:
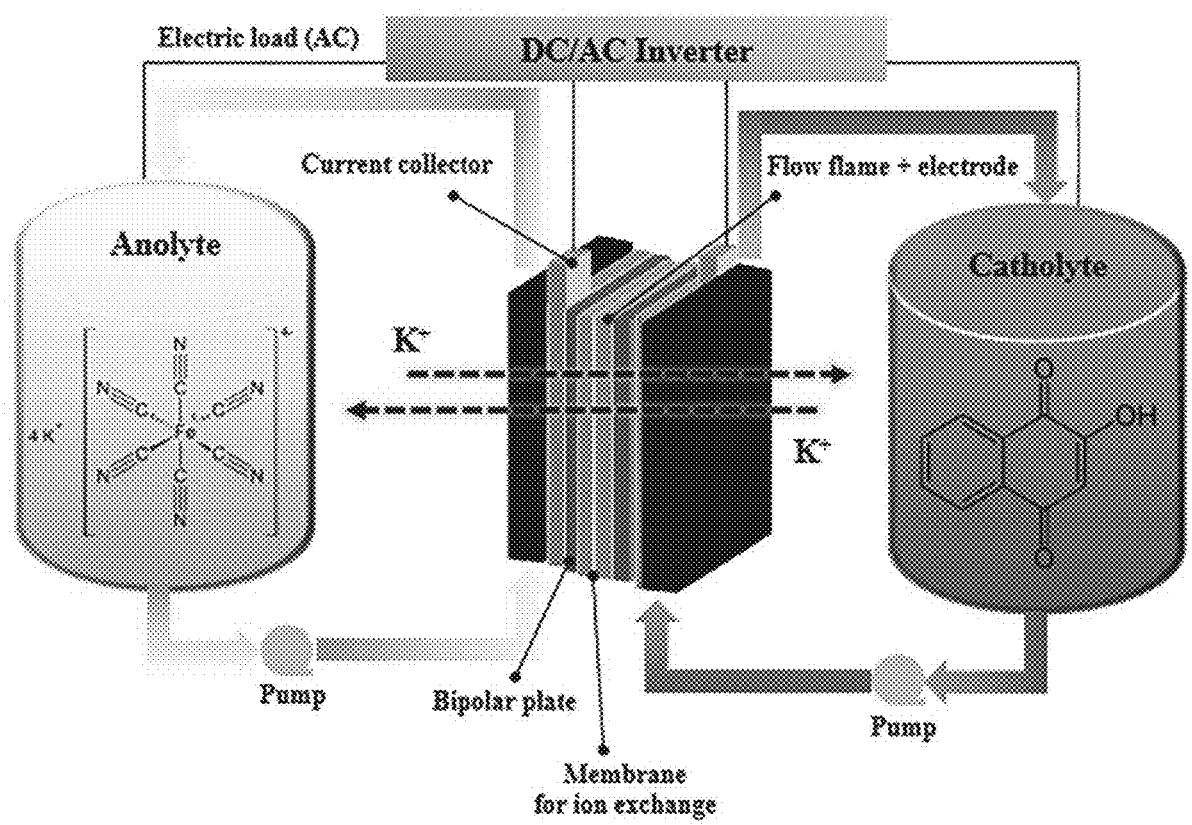
FIG. 7 illustrates a full cell prepared in Experimental Example 5.
Figure 8A:
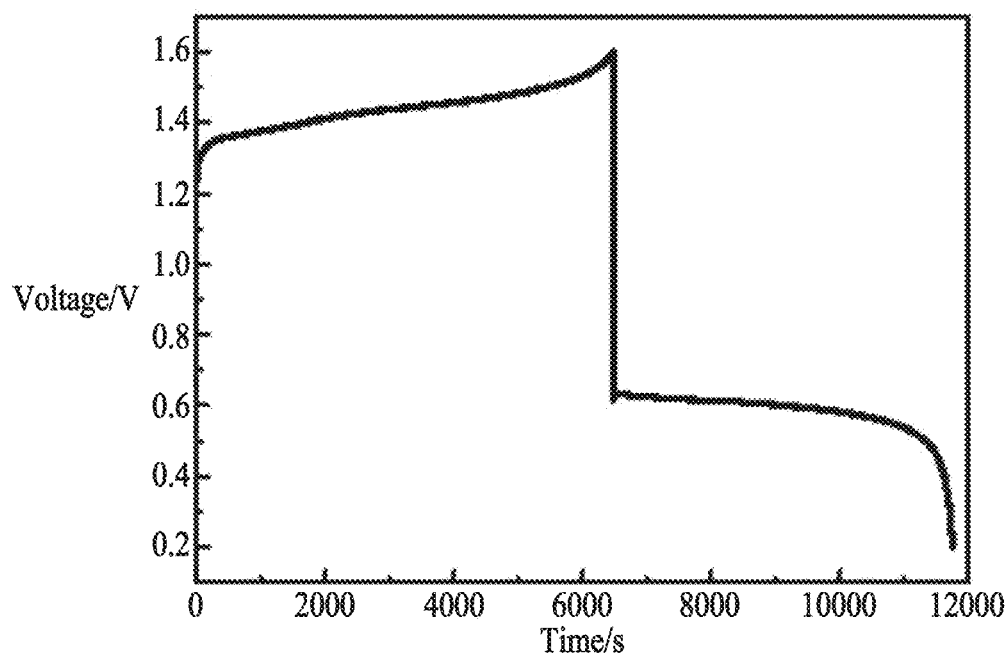
FIGS. 8A, 8B, 8C and 8D illustrate electrode performance of a full cell confirmed in Experimental Example 5; and specifically.
Figure 8B:
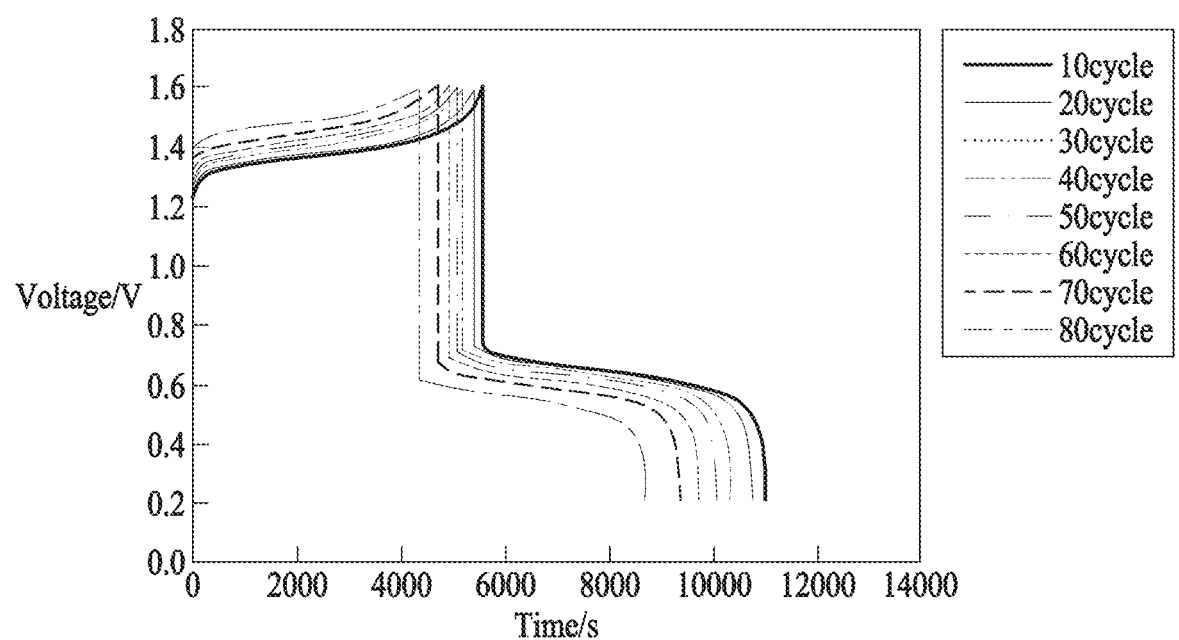
Figure 8C:
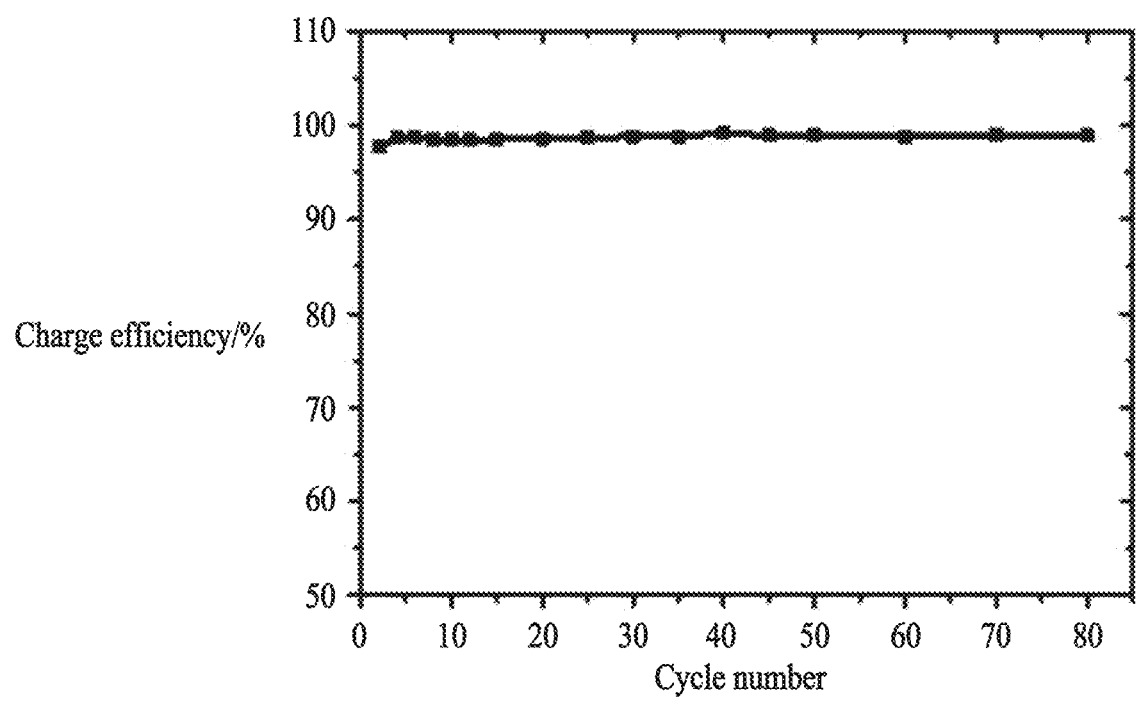
Figure 8D:
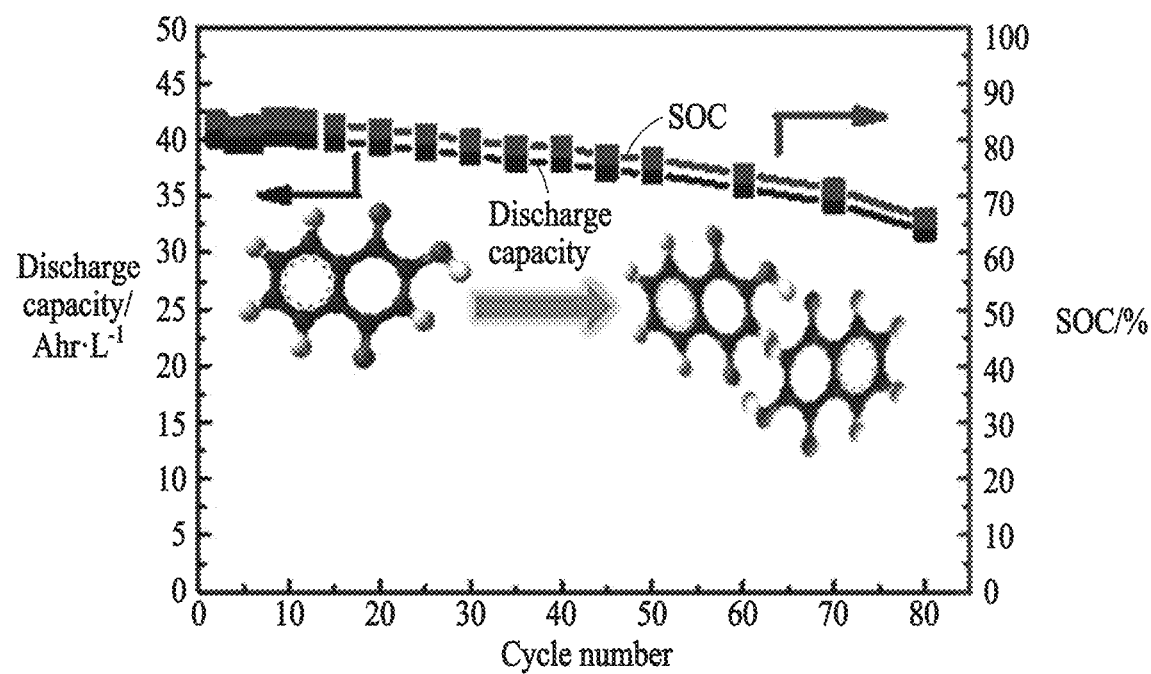

In terms of a cross-over issue, since a molecule size of NQ-SO (4 to 8 mm) is greater than a pore size of Nafion 117 membrane (2.5 nm or less in diameter), a possibility of cross-over of NQ-SO molecules is low. Since FeCN is an anion, there is little possibility of its cross-over through Nafion. Therefore, a cross-over issue of a redox couple may not be a problem. A basic structure of the ARFB using NQ-SO and FeCN is shown in FIG. 7.

In addition, to achieve a higher capacity by a high concentration of NQ-SO, a catholyte was prepared by dissolving 0.4 M FeCN into 120 mL of 1 M KOH. An anolyte was prepared by dissolving 1.2 M NQ-SO (0.4 M NQ-S and 0.8 M Lawsone) in 20 mL of 1 M KOH. All ARFB full cell tests were performed at 100 mA·cm$^{-2}$, and a cut-oﬀ voltage range of ARFB full cells were a range of 0.2 to 1.6 V. To detect a possibility of cross-over and chemical degradation, CV tests, pH, UV-vis, and H-NMR tests were performed before and after the ARFB full cell tests.

In ARFBs using NQ-SO and FeCN, 0.4 M FeCN (anolyte) and a mixture of 0.4 M NQ-S and 0.8 M Lawsone (1.2 M NQ-SO) (catholyte) were prepared with a 1 M KOH solution. The performance of ARFBs operated at 100 mA·cm$^{-2}$ shows a CE of 99%, a capacity decay rate of 0.104 Ah·L$^{-1}$ per cycle during 80 cycles, and a discharge capacity of 40.3 Ah·L$^{-1}$ in a state of charge (SOC) of 83%, as shown in FIGS. 8A to 8D. Although the ARFBs exhibit a very low capacity fade rate (0.0079% per cycle), the capacity only achieved 8.14 Ah·L$^{-1}$ or less in spite of a high Lawsone concentration of 0.7 M. The above result was meaningful, but a capacity decay rate needs to be improved.

Figure 9A:
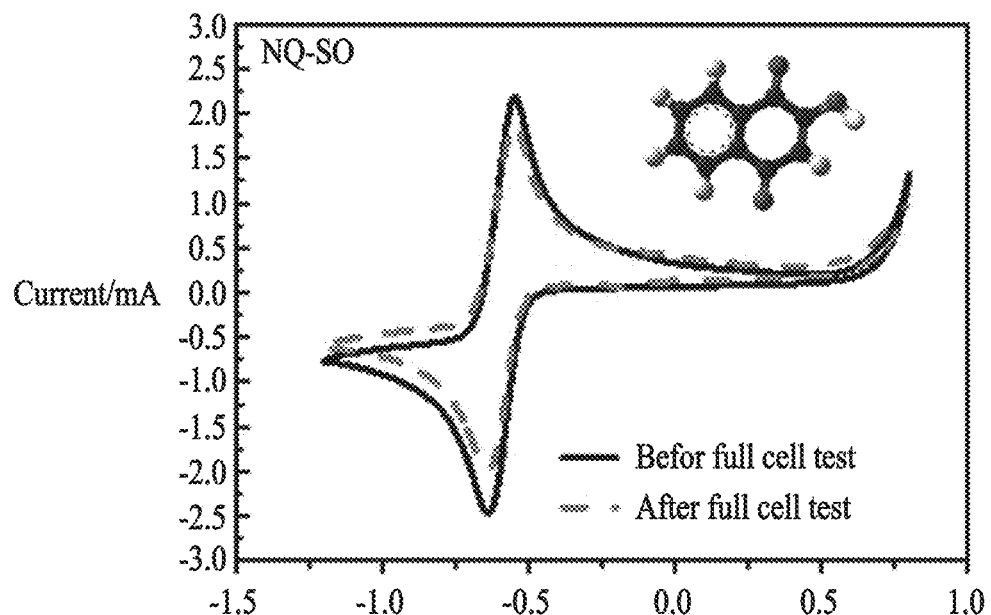
FIGS. 9A and 9B illustrate a comparison of CV curves before and after an aqueous redox flow battery (ARFB) test confirmed in Experimental Example 5.
Figure 9B:
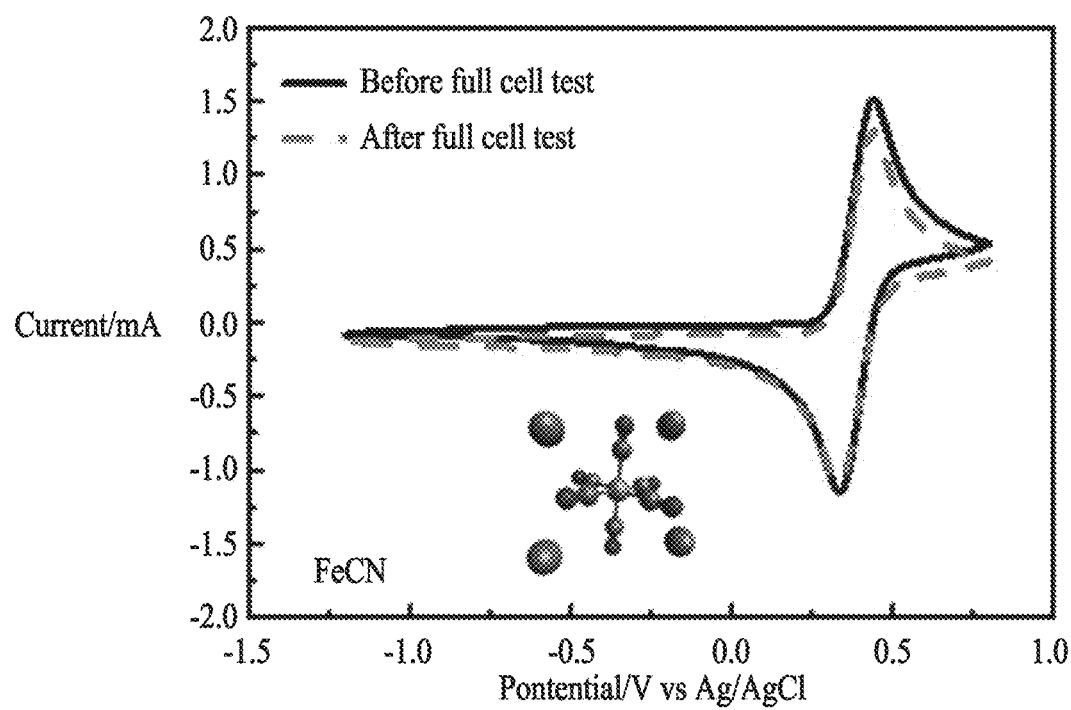
Figure 10:
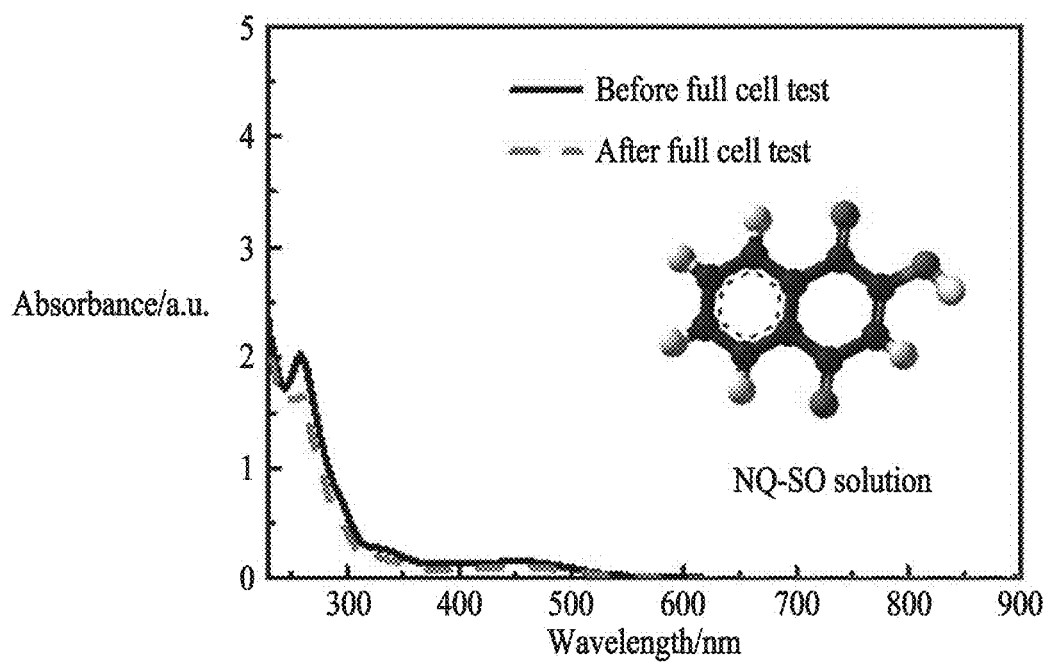
FIG. 10 illustrates an absorbance of an NQ-SO solution before and after the ARFB test confirmed in Experimental Example 5.

Characterizations of "before ARFB test" and "after ARFB test" samples were performed and the results are compared and shown in FIGS. 9A to 10. Specifically, the ARFB test may be performed to observe active materials before and after charging and discharging a full cell fabricated as described above. Through the CV test, whether a permeation phenomenon in which an active material moves to the opposite side has occurred may be determined. According to a CV measurement as shown in FIGS. 9A and 9B, there were no relics of cross-over in both NQ-SO and FeCN during cycling. Even in UV-vis data of NQ-SO as shown in FIG. 10, there was no evidence of cross-over and chemical degradation during cycling. In addition, pH of FeCN and NQ-SO solutions were similar as a weak alkaline even after the ARFB test. This means that the pH of both NQ-SO and FeCN are reversible during cycling and the reversible pH is an evidence that a redox couple works stably during cycling. In contrast, according to H-NMR data of NQ-SO, a peak at 7 to 8 ppm was observed during cycling, which is an evidence that the NQ-SO is dimerized during cycling.

A dimer formation was also proven by CV curves of FIGS. 12A and 12B and was measured at both low and high concentrations of NQ-SO (0.1 M and 0.6 M). When the CV curves of NQ-SO were observed, it may be seen that as the concentration of NQ-SO increases from 0.1 to 0.6 M, a voltage difference at an end point of charge/discharge increases. In other words, it may be found that the overpotential increases as the concentration increases. The overpotential also increases due to an increase in a viscosity and a resistance of electrolytes. For example, when the concentration of NQ-SO increases, the NQ-SO may be dimerized, thereby increasing a viscosity and a resistance and decreasing an electron transfer rate.

To alleviate a capacity decay issue by dimerization occurred during cycling, the concentration of NQ-SO was lowered. To achieve a higher stability (a lower capacity decay) with NQ-SO during cycling, the concentration of NQ-SO decreased from 1.2 M to 0.6 M to have a combination of 0.2 M NQ-S and 0.4 M Lawsone (a 1:2 ratio of NQ-S and Lawsone) in a KOH solution. Performance of an ARFB using 0.4 M FeCN and 0.6 M NQ-SO was compared with that of an ARFB using 0.4 M FeCN and 1.2 M NQ-SO. When the performance of the ARFB using 0.4 M FeCN and 0.6 M NQ-SO was estimated, CE and EE were 99% and 55%. A discharge capacity was 22 Ah·L$^{-1}$ in an SOC of 70%, and a power density was 90 mW·cm$^{-2}$, as shown in FIGS. 11A to 11D. Surprisingly, compared to the performance of the ARFB using 0.4 M FeCN and 1.2 M NQ-SO of FIGS. 8A to 8D, its capacity decay rate was far more improved as 0.006 Δh·L$^{-1}$ during "200" cycles. For such an excellent cycle stability, dimerization of NQ-SO may be suppressed by the use of a low 0.6 M NQ-SO. When the ARFB using 0.4 M FeCN and 0.6 M NQ-SO was operated, no side reactions were observed in NQ-SO during cycling.

Although the example embodiments have been described by limited drawings as described above, a person having ordinary skill in the art may apply various modifications and changes based on the example embodiments. For example, although described techniques are performed in a different order from a described method, and/or described elements such as systems, structures, devices, and circuits are combined or merged in a different form from the described method, or replaced or substituted with other elements or equivalents, appropriate results may be achieved.

Therefore, equivalents to other example embodiments, other example embodiments, and patent claims are also belong to the scope of claims to be described below.

What is claimed is:

1. An electrolyte for an aqueous redox flow battery (ARFB), the electrolyte comprising a mixture of a compound represented by Formula (I) and a compound represented by Formula (II):

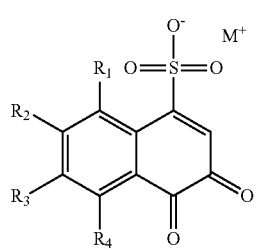

(I)

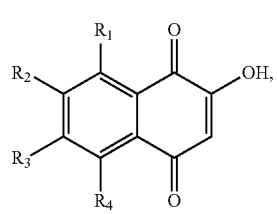

(II)

wherein

R$_1$ to R$_4$ are each independently selected from the group consisting of hydrogen, halogen, C$_1$-C$_3$ alkyl, and C$_1$-C$_3$ alkoxy, and M is a metal selected from the group consisting of Na, Li, and K;

wherein the electrolyte is a basic aqueous solution.

2. The electrolyte of claim 1, wherein a molar ratio of the compound represented by Formula (II) to the compound represented by Formula (I) ranges from 0.1 to 10.

3. The electrolyte of claim 1, wherein the compound represented by Formula (I) has a lower molar concentration than the compound represented by Formula (II).

4. The electrolyte of claim 1, wherein a molar ratio of the compound represented by Formula (II) to the compound represented by Formula (I) ranges from 1.5 to 3.

5. The electrolyte of claim 1, wherein the compound represented by Formula (I) is a compound represented by Formula (III):

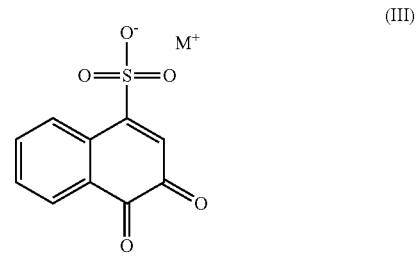

(III)

wherein M is the same as defined in claim 1.

6. The electrolyte of claim 1, wherein the compound represented by Formula (II) is a compound represented by Formula (IV):

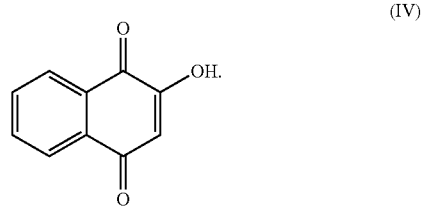 [SMILES: O=C1C=C(O)C(=O)c2ccccc21]

(IV)

7. The electrolyte of claim 1, wherein the electrolyte contains KOH.

8. An aqueous redox flow battery (ARFB) comprising the electrolyte of claim 1.

9. The ARFB of claim 8, wherein the electrolyte is used as a negative electrode electrolyte and ferrocyanide is used as a positive electrode electrolyte.

* * * * *